United States Patent
Amancha et al.

(10) Patent No.: US 11,975,096 B2
(45) Date of Patent: *May 7, 2024

(54) LIQUID NALOXONE SPRAY

(71) Applicant: HIKMA PHARMACEUTICALS USA INC., Eatontown, NJ (US)

(72) Inventors: Kiran Amancha, Chandler, AZ (US); Chandeshwari Chilampalli, Chandler, AZ (US); Thrimoorthy Potta, Phoenix, AZ (US); Ningxin Yan, Chandler, AZ (US); Venkat R. Goskonda, Phoenix, AZ (US)

(73) Assignee: Hikma Pharmaceuticals USA Inc., Berkeley Heights, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/411,507

(22) Filed: Aug. 25, 2021

(65) Prior Publication Data

US 2023/0008410 A1    Jan. 12, 2023

Related U.S. Application Data

(63) Continuation of application No. 16/177,361, filed on Oct. 31, 2018, now Pat. No. 11,135,155, which is a continuation-in-part of application No. 15/876,553, filed on Jan. 22, 2018, now Pat. No. 10,441,538, which is a continuation-in-part of application No. 15/601,331, filed on May 22, 2017, now Pat. No. 10,617,686, which is a continuation-in-part of application No. 15/238,909, filed on Aug. 17, 2016, now Pat. No. 10,722,510, which is a continuation-in-part of application No. 15/076,080, filed on Mar. 21, 2016, now abandoned, which is a continuation-in-part of application No. 14/730,585, filed on Jun. 4, 2015, now Pat. No. 9,642,848.

(60) Provisional application No. 62/022,041, filed on Jul. 8, 2014.

(51) Int. Cl.
| | |
|---|---|
| *A61K 9/00* | (2006.01) |
| *A61K 9/08* | (2006.01) |
| *A61K 31/485* | (2006.01) |
| *A61K 47/02* | (2006.01) |
| *A61K 47/10* | (2017.01) |
| *A61K 47/12* | (2006.01) |
| *A61K 47/18* | (2017.01) |
| *A61P 25/36* | (2006.01) |

(52) U.S. Cl.
CPC ............ *A61K 9/0043* (2013.01); *A61K 9/006* (2013.01); *A61K 9/08* (2013.01); *A61K 31/485* (2013.01); *A61K 47/02* (2013.01); *A61K 47/10* (2013.01); *A61K 47/12* (2013.01); *A61K 47/183* (2013.01); *A61P 25/36* (2018.01)

(58) Field of Classification Search
CPC .... A61K 31/485; A61K 9/0043; A61K 47/10; A61K 47/02; A61K 47/12; A61K 47/18
See application file for complete search history.

(56) References Cited

U.S. PATENT DOCUMENTS

| | | |
|---|---|---|
| 4,416,886 A | 11/1983 | Bernstein |
| 4,626,539 A | 12/1986 | Aungst |
| 4,782,047 A | 11/1988 | Benjamin et al. |
| 5,866,154 A | 2/1999 | Bahal et al. |
| 5,897,858 A | 4/1999 | Haslwanter et al. |
| 6,677,346 B1 | 1/2004 | Achari |
| 7,214,318 B2 | 5/2007 | Suzuki et al. |
| 8,216,604 B2 | 7/2012 | Watts et al. |
| 8,399,508 B2 | 3/2013 | Singh et al. |
| 9,192,570 B2 * | 11/2015 | Wyse ................... A61K 9/0043 |
| 9,211,253 B2 * | 12/2015 | Crystal ..................... A61P 9/00 |
| 9,642,848 B2 * | 5/2017 | Amancha ................. A61K 9/12 |
| 10,441,538 B2 * | 10/2019 | Amancha ............. A61K 31/485 |
| 10,617,686 B2 * | 4/2020 | Amancha ................. A61K 9/08 |
| 10,722,510 B2 * | 7/2020 | Amancha ................. A61K 9/08 |
| 10,973,814 B2 * | 4/2021 | Amancha ............. A61K 47/10 |
| 11,135,155 B2 * | 10/2021 | Amancha ............. A61K 47/183 |
| 11,617,713 B2 * | 4/2023 | Amancha ............. A61K 31/485 |
| | | 514/282 |

(Continued)

FOREIGN PATENT DOCUMENTS

| | | |
|---|---|---|
| CN | 1303674 | 7/2001 |
| CN | 1575795 | 2/2005 |

(Continued)

OTHER PUBLICATIONS

G.W. Pasternak, et al., "Selective Enhancement of [3H]Opiate Agonist Binding by Divalent Cations," Molecular Pharmacology, vol. 11, pp. 735-744 (1975).

G.B. Drummond, et al., "Naloxone: Dose-Dependent Antagonism Of Respiratory Depression By Fentanyl In Anaesthetized Patients," British J. Anaesth., vol. 49, pp. 151-154 (1977).

The Merck Index: An Encyclopedia of Chemicals, Drugs, and Biologicals, pp. MISC-47-MISC-60 (Merck & Co., 10th ed., 1983) ("Merck Index").

T.W. Rosanske, Chemical Stability of Pharmaceuticals: A Handbook for Pharmacists, pp. 604-611 (K.A. Connors, et al., eds., 2nd ed., 1986).

(Continued)

*Primary Examiner* — James D. Anderson
(74) *Attorney, Agent, or Firm* — Wood, Phillips, Katz, Clark & Mortimer

(57) ABSTRACT

The invention provides stable liquid formulations containing naloxone, a pharmaceutically acceptable salt or a derivative thereof. The invention further provides methods for treating opioid overdose, opioid dependence, and congenital insensitivity to pain with anhidrosis by administering the liquid formulations of the present invention intranasally to a patient in need thereof. Further, the invention provides a method of treating opioid dependence, opioid overdose, and congenital insensitivity to pain with anhidrosis by administering intranasally the naloxone formulations of the present invention.

19 Claims, 1 Drawing Sheet

(56) References Cited

U.S. PATENT DOCUMENTS

| | | | |
|---|---|---|---|
| 11,628,139 B2* | 4/2023 | Amancha | A61K 31/485 514/282 |
| 2002/0037297 A1 | 3/2002 | Crespo et al. | |
| 2003/0185761 A1 | 10/2003 | Dugger | |
| 2005/0153946 A1 | 7/2005 | Hirsh et al. | |
| 2007/0261695 A1 | 11/2007 | Kottayil et al. | |
| 2007/0293581 A1 | 12/2007 | Malcom | |
| 2009/0041687 A1 | 2/2009 | Beumer et al. | |
| 2009/0325857 A1 | 12/2009 | Beumer et al. | |
| 2011/0023870 A1 | 2/2011 | Wermeling | |
| 2012/0070495 A1 | 3/2012 | Shah et al. | |
| 2012/0217184 A1 | 8/2012 | Edwards et al. | |
| 2013/0071477 A1 | 3/2013 | Fischer | |
| 2014/0171458 A1 | 6/2014 | Brown et al. | |
| 2015/0071971 A1 | 3/2015 | Amancha et al. | |
| 2016/0008277 A1 | 1/2016 | Crystal et al. | |
| 2016/0008349 A1 | 1/2016 | Amancha et al. | |
| 2016/0199294 A1 | 7/2016 | Amancha et al. | |
| 2016/0354363 A1 | 12/2016 | Amancha et al. | |
| 2017/0252337 A1 | 9/2017 | Amancha et al. | |

FOREIGN PATENT DOCUMENTS

| | | |
|---|---|---|
| CN | 1726915 | 2/2006 |
| CN | 101057830 | 10/2007 |
| EP | 0780127 | 6/1997 |
| EP | 0913152 | 5/1999 |
| EP | 0880352 | 11/1999 |
| EP | 1681057 | 7/2006 |
| WO | 0035456 | 6/2000 |
| WO | 0062757 | 10/2000 |
| WO | 0076474 | 12/2000 |
| WO | 03105856 | 12/2003 |
| WO | 2006058022 | 6/2006 |
| WO | 2012094283 | 7/2012 |
| WO | 2012156317 | 11/2012 |
| WO | 2014071499 | 5/2014 |

OTHER PUBLICATIONS

R. Panchagnula, et al., "Transdermal delivery of naloxone: effect of water, propylene glycol, ethanol and their binary combinations on permeation through rat skin," Int'l J Pharmaceutics, vol. 219, pp. 95-105 (2001).

M.A. Quarry, et al., "Investigation of 4,5-epoxymorphinan degradation during analysis by HPLC," J Pharmaceutical and Biomedical Analysis, vol. 30, pp. 99-104 (2002).

FDA, Guidance for Industry: Nasal Spray and Inhalation Solution, Suspension, and Spray Drug Products—Chemistry, Manufacturing, and Controls Documentation (Jul. 2002).

E.D. Barton, et al., "Intranasal Administration of Naloxone by Paramedics," Prehospital Emergency Care, vol. 6, pp. 54-58 (2002) ("Barton 2002").

E.D. Barton, et al., "Efficacy Of Intranasal Naloxone As A Needleless Alternative For Treatment Of Opioid Overdose In The Prehospital Setting," J Emergency 1'.!ed, vol. 29, pp. 265-271 (2005).

E.L.A. van Dorp, et al., "Naloxone treatment in opioid addiction: the risks and benefits," Expert Opin. Drug Saf, vol. 6, pp. 125-132 (2007).

The United States Pharmacopeia, 2008 USP 31/NF 26, vols. 2-3, pp. 2039, 2752-53 (The United States Pharmacopeial Convention, 2007).

T.L. Lemke et al., Foye's Principles of Medicinal Chemistry, p. 670 (6th ed., 2008).

A. Jouyban, "Review of the cosolvency models for predicting solubility of drugs in water-cosolvent mixtures," J Phann. Pharmaceut. Sci., vol. 11, pp. 32-58 (2008) ("Jouyban").

R.C. Rowe, et al., eds., Handbook of Pharmaceutical Excipients, pp. 17-19, 242-44, 247-50, 592-94, 766-70 (Pharmaceutical Press, 6th ed., 2009).

D. Kerr, et al., "Randomized controlled trial comparing the effectiveness and safety of intranasal and intramuscular naloxone for the treatment of suspected heroin overdose," Addiction, vol. 104, pp. 2067-2074 (2009).

S.B. Leavitt, "Intranasal Naloxone for At-Home Opioid Rescue," Practical Pain Manageme:nt, vol. 10, pp. 42-46 (2010).

D.P. Wermeling, "Opioid Harm Reduction Strategies: Focus on Expanded Access to Intranasal Naloxone," Pharmacotherapy, vol. 30, pp. 627-631 (2010).

S.K.S. Kushwaha, et al., "Advances in nasal trans-mucosal drug delivery," J. Applied Pharm. Sci., vol. 1(7), pp. 21-28 (2011) ("Kushwaha");.

C. Bitter, et al., "Nasal Drug Delivery in Humans," Curr. Prob !. Dermatol., vol. 40, pp. 20-35 (2011).

L.S. Middleton, et al., "The phannacodynamic and phannacokinetic profile of intranasal crushed buprenorphine and buprenorphine/naloxone tablets in opioid abusers," Addiction, vol. 106, pp. 1460-1473 (2011).

FDA, "Role of Naloxone in Opioid Overdose Fatality Prevention; Public Workshop; Request for Comments," 76 Fed. Reg. 71348 (Nov. 17, 2011).

V. Kulkami, et al., "Formulation and characterization of nasal sprays: An examination of nasal spray formulation parameters and their influence on key in vitro tests," Inhalation, pp. 10-15 (Jun. 2012).

The United States Pharmacopeia, 2013 USP 36/NF 21, pp. 54-55, 930-33 (The United States Phannacopeial Convention, 2012).

D.P. Wermeling, "A response to the opioid overdoes epidemic: naloxone nasal spray," Drug Deliv. and Transl. Res., vol. 3, pp. 63-74 (2013).

P.G. Djupesland, "Nasal drug delivery devices: characteristics and performance in a clinical perspective-a review," Drug Deliv. and Transl. Res., vol. 3, pp. 42-62 (2013).

A.Y. Walley, et al., "Opioid overdose rates and implementation of overdose education and nasal naloxone distribution in Massachusetts: interrupted time series analysis," British Med. J, vol. 346, pp. 1-13 (2013).

FDA, Inactive Ingredient Guide (Mar. 2013), available at: https://wayback.archive-it.org/7993/20170406031208/ https://www.fda.gov/Drugs/InformationOnDrugs/ucml 13978.htm.

Labeling for Narcan (naloxone hydrochloride injection, USP) Injection (0025223), published Jul. 2003, and obtained from https://www.accessdata.fda.gov/drugsatfda_docs/label/2002/016636s052s054lbl.pdf on Mar. 5, 2024.

Labeling for Evzio (naloxone hydrochloride injection) 0.4mg Auto-Injector (NDA 205787), published Apr. 2014 and obtained from https://www.accessdata.fda.gov/drugsatfda_docs/nda/2014/205787Orig1s000Approv.pdf on Mar. 4, 2024.

Labeling for Narcan (naloxone hydrochloride) 4mg Nasal Spray (NDA 208411), published Nov. 2015 and obtained from https://www.accessdata.fda.gov/drugsatfda_docs/label/2015/208411lbl.pdf on Mar. 4, 2024.

Labeling for Evzio (naloxone hydrochloride injection) 2mg Auto-Injector (NDA 209862), published Oct. 2016 and obtained from https://www.accessdata.fda.gov/drugsatfda_docs/nda/2016/209862Orig1s000Approv.pdf on Mar. 4, 2024.

* cited by examiner

LIQUID NALOXONE SPRAY

FIELD OF THE INVENTION

The invention is directed to liquid spray formulations containing naloxone, a pharmaceutically acceptable salt thereof, or a derivative thereof. The invention is further directed to methods of treating opioid overdose, opioid dependence, and congenital insensitivity to pain with anhidrosis by administering liquid spray formulations containing naloxone, pharmaceutically acceptable salts thereof, or derivatives thereof to a patient in need thereof.

BACKGROUND OF THE INVENTION

Naloxone has the following structure and is synthesized from thebaine:

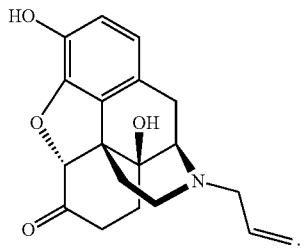

Naloxone is most commonly used to treat patients suffering from opioid dependence or overdose because it is a competitive µ-opioid antagonist that blocks the effects of opioids. Naloxone is currently available in Suboxone® (Suboxone is a registered trademark of Reckitt Benckiser Healthcare (UK) Limited) as tablet or sublingual film strip formulations. Suboxone® contains buprenorphine and naloxone in a 4:1 ratio. Naloxone is also available as an aqueous nasal spray under the trademark Narcan® (Narcan is a registered trademark of Adapt Pharma Operations Limited LLC, "Adapt Pharma"), which contains 4.42% w/w naloxone hydrochloride dihydrate, 0.01% w/w benzalkonium chloride ("BKC") as a preservative, 0.74% w/w sodium chloride as an isotonicity agent and 0.2% w/w edetate disodium dihydrate ("EDTA") as a stabilizing agent. Adapt Pharma has U.S. Pat. Nos. 9,211,253, 9,468,747 and 9,561,117 listed in the U.S. Food and Drug Administration's Orange Book for Narcan® 4 milligram nasal spray. Each of these patents discloses and claims naloxone formulations containing an isotonicity agent. Additional Adapt Pharma also has U.S. Pat. No. 9,480,644 listed in the Orange Book for a 2-milligram naloxone nasal spray, which discloses and claims naloxone formulations that also contain an isotonicity agent. U.S. Pat. Nos. 9,192,570 and 9,289,425 assigned to Indivior, Inc disclose and claim naloxone nasal sprays that contain both citric acid as a buffer and benzyl alcohol as an anti-microbial agent.

One issue with other opioid dependence treatments is that they can become addictive. Naloxone, however, does not appear to be addictive and patients do not build up a tolerance.

Naloxone has also been used as a treatment for cognitive insensitivity to pain with anhidrosis. Insensitivity to pain with cognitive anhidrosis is a disorder in which the patient cannot feel pain.

Naloxone may be administered orally, intravenously, by injection or via the nasal mucosa. Naloxone has a low mean serum half-life when administered parentally. The quick metabolism may require repeat dosing or cause patient discomfort between doses. Enteral administration has low bioavailability due to hepatic first pass metabolism.

Accordingly, while there are some naloxone formulations currently available, there is a need for safe and effective liquid spray formulations that are stable including physically and chemically stable and contain naloxone, pharmaceutically acceptable salts or a derivative thereof.

SUMMARY OF THE INVENTION

The liquid spray formulations of the present invention are for intranasal and/or sublingual administration.

In one aspect, the invention is directed to liquid spray formulations comprising an effective amount of naloxone, a pharmaceutically acceptable salt thereof, or a derivative thereof, water, and a chelating agent, wherein the formulation does not contain an isotonicity agent or a buffer.

In another aspect, the stable liquid spray formulations of the present invention are suitable for intranasal administration.

In another aspect, the liquid spray formulations of the present invention do not contain an isotonicity agent.

In another aspect, the liquid spray formulations of the present invention do not contain sodium chloride.

In another aspect, the liquid spray formulations of the present invention do not contain benzalkonium chloride.

In another aspect, the liquid spray formulations of the present invention do not contain a buffer.

In another aspect, the liquid spray formulations of the present invention do not contain citric acid.

In another aspect, the liquid spray formulations of the present invention do not contain an alcohol.

In a further aspect, the invention is directed to methods for treating opioid overdose comprising administering the liquid spray formulations of the present invention to a patient in need of opioid overdose treatment, wherein administration occurs either intranasally, sublingually or intranasally and sublingually, wherein if administration occurs intranasally and sublingually administration occurs simultaneously, sequentially or concomitantly.

In yet another aspect, the invention is directed to methods for treating opioid dependence comprising administering the liquid spray formulations of the present invention to a patient in need of opioid dependence treatment, wherein administration occurs either intranasally, sublingually or intranasally and sublingually, wherein if administration occurs intranasally and sublingually administration occurs simultaneously, sequentially or concomitantly.

In an additional aspect, the invention is directed to methods for treating congenital insensitivity to pain with anhidrosis comprising administering the liquid spray formulations of the present invention to a patient in need of treatment for congenital insensitivity to pain with anhidrosis, wherein administration occurs either intranasally, sublingually or intranasally and sublingually, wherein if administration occurs intranasally and sublingually administration occurs simultaneously, sequentially or concomitantly.

In a further aspect, the invention is directed to a nasal spray formulation comprising naloxone, a pharmaceutically acceptable salt thereof, or a derivative thereof, wherein the formulation provides improved pharmacokinetic parameters when administered intranasally versus administration via intramuscular injection or intravenous injection.

DETAILED DESCRIPTION OF THE INVENTION

Figure 1:
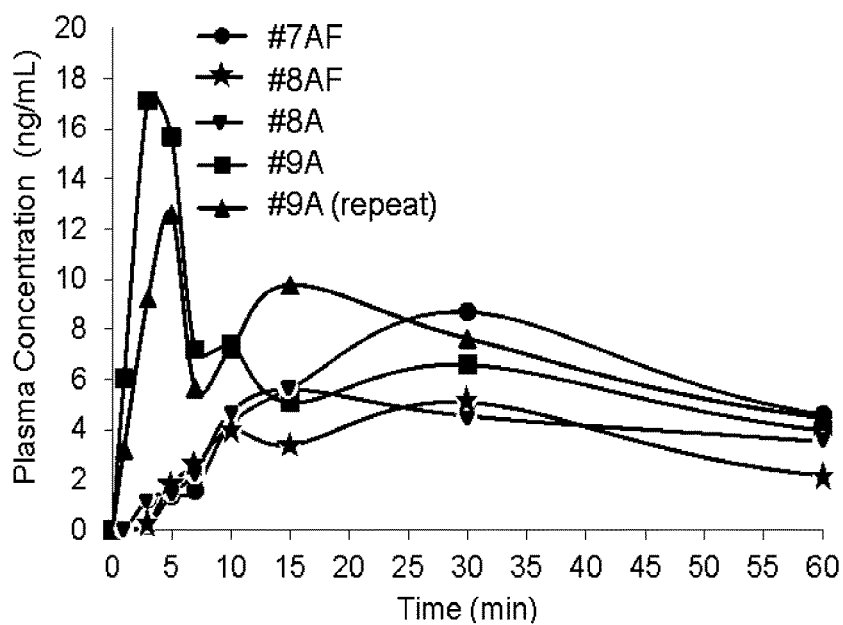
FIG. 1. Mean plasma concentration of Formulations #9A, #9A repeat #8A, #8AF and #7AF normalized to a 4-mg dosage. Values based on a geometric mean.

Applicants have created new liquid naloxone formulations that are stable and comfortable to the user despite containing no buffer or isotonicity agent. The formulations that do not contain an alcohol are especially suitable for administration to children. Further, the alcohol-free formulations may be suitable for patients in recovery from alcohol addiction.

In a preferred embodiment, the liquid naloxone formulation is a spray. In yet a more preferred embodiment, the liquid naloxone formulation is in a simple solution form. As used herein, the term "simple solution" refers to a solution in which the solute(s) has fully dissolved in the solvent.

As used herein, the term "stable" includes but is not limited physical and chemical stability.

In one embodiment, the present invention is directed to liquid spray formulations comprising an effective amount of naloxone, a pharmaceutically acceptable salt thereof, or a derivative thereof, water, and a chelating agent, wherein the formulation does not contain an isotonicity agent or a buffer.

In another embodiment, the liquid spray formulations of the present invention is for intranasal administration.

In another embodiment, the liquid spray formulations of the present invention do not contain sodium chloride, citric acid, benzyl alcohol, or benzalkonium chloride.

In another embodiment, the present invention is directed to liquid spray formulations comprising an effective amount of naloxone, a pharmaceutically acceptable salt thereof, or a derivative thereof, a co-solvent selected from the group consisting of an alcohol, a glycol, and a combination thereof water, and edetate disodium dihydrate as a chelating agent, wherein the formulation does not contain an isotonicity agent or a buffer.

In another embodiment, the present invention is directed to liquid spray formulations comprising an effective amount of naloxone, a pharmaceutically acceptable salt thereof, or a derivative thereof, a co-solvent selected from the group consisting of an alcohol, a glycol, and a combination thereof water, and edetate disodium dihydrate as a chelating agent, wherein the formulation does not contain an isotonicity agent or a buffer, wherein the alcohol is ethanol (dehydrated alcohol) and the glycol is propylene glycol.

In another embodiment, the liquid spray formulations of the present invention have a pH from about 3.0 to about 6.0, more preferably about 4.5.

In another embodiment, the present invention is directed to liquid spray formulations comprising an effective amount of naloxone, a pharmaceutically acceptable salt thereof, or a derivative thereof, water, a chelating agent, and an antioxidant, preferably sodium ascorbate, wherein the formulation does not contain an isotonicity agent or a buffer.

In another embodiment, the present invention is directed to liquid spray formulations comprising:
from about 1% to about 16% w/w naloxone, a pharmaceutically acceptable salt or a derivative thereof, preferably from about 2% to about 10% w/w;
from about 10% to about 99% w/w water;
from about 0.0001% to 0.05% w/w of a chelating agent, preferably edetate disodium dehydrate,
wherein the formulation does not contain an isotonicity agent or a buffer.

In another embodiment, the liquid spray formulations of the present invention do not contain an alcohol.

In another embodiment, the present invention is directed to liquid spray formulations comprising:
from about 1% to about 16% w/w naloxone, a pharmaceutically acceptable salt or a derivative thereof, preferably from about 2% to about 10% w/w;
from about 80% to about 98% w/w water;
from about 0.0001% to 0.05% w/w of a chelating agent, preferably edetate disodium dihydrate,
wherein the formulation does not contain an isotonicity agent, a buffer or a co-solvent.

In another embodiment, the present invention is directed to liquid spray formulations comprising:
from about 1% to about 16% w/w naloxone, a pharmaceutically acceptable salt or a derivative thereof, preferably from about 2% to about 10% w/w;
from about 35% to about 85% w/w water;
from about 0.0001% to 0.05% w/w of a chelating agent, preferably edetate disodium dihydrate; and
from about 2% to about 90% w/w of a co-solvent selected from the group consisting of ethanol, propylene glycol and a combination thereof, preferably ethanol at a concentration from about 2% to about 50% w/w, or a combination of propylene glycol at a concentration from about 5% to about 10% w/w and ethanol at a concentration from about 2% to about 50% w/w or a combination of ethanol at about 20% w/w and propylene glycol at about 5% w/w or a combination of ethanol at about 50 w/w and propylene glycol at about 5% w/w,
wherein the formulation does not contain an isotonicity agent or a buffer.

In another embodiment, the present invention is directed to liquid spray formulations comprising
from about 1% to about 16% w/w naloxone, a pharmaceutically acceptable salt or a derivative thereof, preferably from about 2% to about 10% w/w;
from about 35% to about 85% w/w water;
from about 0.0001% to 0.05% w/w of a chelating agent, preferably edetate disodium dihydrate; and
propylene glycol as a co-solvent at a concentration from about 5% to about 10% w/w,
wherein the formulation does not contain an isotonicity agent, a buffer or an alcohol.

In another embodiment, the liquid spray formulations of the present invention comprise a preservative selected from the group consisting of butyl paraben, methyl paraben, ethyl paraben, propyl paraben, sodium benzoate, benzoic acid and a combination thereof, preferably from about 0.005% to about 0.2% w/w methyl paraben and more preferably 0.1% w/w methyl paraben.

In another embodiment, the liquid spray formulations of the present invention do not contain a preservative.

In another embodiment, the liquid spray formulations of the present invention are administered in a nasal spray device.

In another embodiment, the liquid spray formulations of the present invention are administered in a nasal spray device that is capable of producing a droplet size distribution wherein greater than 90% of the composition particles are greater than 10 microns in diameter during administration or a droplet size distribution wherein:

the mean Dv(10) is from about 5 to about 40 microns during administration;

the mean Dv(50) is from about 20 to about 80 microns during administration; and the mean Dv(90) is from about 50 to about 700 microns during administration, or a spray plume that has an ovality ratio of from about 1.0 to 2.5, or a spray plume width from about 25 to about 70 millimeters during administration and a spray plume angle from about 15 to about 70 degrees during administration.

In another embodiment, the liquid spray formulations of the present invention are administered in a nasal spray device that has a single reservoir comprising about 125 µl to 127 µL of the formulation.

In another embodiment, the liquid spray formulations of the present invention are administered in a nasal spray device that delivers about 100 µL of the formulation by a single actuation.

Formulations with an Alcohol

In one embodiment, the invention is directed to liquid spray formulations comprising an effective amount of naloxone, a pharmaceutically acceptable salt or a derivative thereof, water as a solvent, a co-solvent and an antioxidant or chelating agent. In a preferred embodiment, naloxone is in salt form.

In another embodiment, the invention is directed to liquid spray formulations comprising an effective amount of naloxone, a pharmaceutically acceptable salt or a derivative thereof, water as a solvent, a co-solvent and a permeation enhancer or chelating agent. In a preferred embodiment, naloxone is in salt form.

The co-solvent may be an alcohol, a glycol, or a mixture thereof. The formulations preferably contain from about 5 to about 90% w/w co-solvent. More preferably the formulations contain from about 10% to about 70% w/w from about 10% to about 55% w/w or from about 40% to about 65% w/w or from about 45% to about 60% w/w or from about 45% to about 55% w/w co-solvent. In a preferred embodiment, the formulations contain about 10% w/w, about 12% w/w, about 25% w/w or about 55% w/w co-solvent. In a more preferred embodiment, the formulations contain about 10% w/w ethanol as a co-solvent or about 2% to about 45% ethanol as a co-solvent, or about 10% to about 20% ethanol as a co-solvent, or about 10% w/w propylene glycol and about 2% w/w ethanol as a co-solvent or about 20% w/w ethanol and about 5% w/w propylene glycol as a co-solvent or about 50% w/w ethanol and 5 w/w propylene glycol as co-solvent.

Alcohol may be preset in formulation of the present invention at a concentration from about 2% to about 90% w/w, from about 10% to about 80% w/w, from about 20% to 50% w/w or at about 20% or 50% w/w.

Propylene glycol may be preset in formulation of the present invention at a concentration from about 1% to about 50% w/w and from about 2% to about 20% w/w.

Suitable antioxidants include butylated hydroxyanisole (BHA), butylated hydroxytoluene (BHT), methionine, sodium ascorbate, sodium thiosulfate, thioglycerol, ascorbic acid, ascorbyl palmitate, propyl gallate, dL-alpha-tocopherol, sodium sulfite, sodium metabisulfite, sodium bisulfate cysteine hydrochloride, glutathione and a combination thereof. Presently preferred antioxidants include BHA, BHT, sodium thiosulfate, dL alpha-tocopherol (Vitamin E) and sodium ascorbate.

In a preferred embodiment, the amount of antioxidant included in the formulation is from about 0.001% to about 0.5% w/w.

In another preferred embodiment, the amount of antioxidant is about 0.01% w/w of BHA.

In an alternative embodiment, the antioxidant is a mixture of about 0.01% w/w of BHA and about 0.005% w/w of BHT.

In yet another embodiment, the antioxidant is about 0.01% w/w of sodium thiosulfate.

In a preferred embodiment, the antioxidant is about 0.3% w/w dL alpha-tocopherol.

In a most preferred embodiment, the antioxidant is about 0.02% w/w of sodium ascorbate.

In the present formulations, water is used as the solvent. Preferably, formulations of the present invention contain from about 10% to about 99% w/w water, more preferably, from about 10% to about 98% w/w water, more preferably from about 35% to about 85% w/w, more preferably from about 35% to about 84% w/w and more preferably about 29.8%, 33.2%, 31.32%, 34.5%, or 35.5%, 37.5%, 65.2%, 71.1%, 79.3%, 81.1%, or 83.9% w/w water. Hydro-alcohol formulations of the present invention preferably contain from about 40% to about 90% w/w water, more preferably, from about 50% to about 90% w/w water. In preferred embodiments, hydro-alcoholic formulations contain about from about 30% to about 80% w/w water.

In a preferred embodiment, the formulations of the present invention have a pH of from about 2 to about 7. In a more preferred embodiment, the formulations of the present invention have a pH of from about 3 to about 6, even more preferably from about 3 to about 4.5.

In a most preferred embodiment, the formulations of the present invention have a pH of about 3.0±0.2 or 3.5±0.2 or 4.0±0.2 or 4.5±0.2.

In another preferred embodiment, the formulations contain ethanol as the co-solvent.

In yet another preferred embodiment, the formulations contain propylene glycol as the co-solvent.

In a more preferred embodiment, the formulations contain a mixture of ethanol and propylene glycol as the co-solvent.

In another embodiment, the formulations of the present invention contain a chelating agent. In a preferred embodiment, the chelating agent is edetate disodium dihydrate, (also known as edetate disodium or ethylenediaminetetraacetic acid disodium salt or EDTA) preferably at a concentration from about 0.0001% to about 0.5% w/w and more preferably from about 0.001% to about 0.05% w/w and even more preferably from about 0.005% to about 0.05% w/w, even more preferably from about 0.001% to about 0.02% w/w and even more preferably from about 0.005% to about 0.01% w/w.

In a preferred embodiment, the present invention is directed to liquid spray formulations comprising naloxone, a pharmaceutically acceptable salt or a derivative thereof, in an amount from about 1% to about 16% w/w, water in an amount from about 10% to about 95% w/w, a co-solvent in an amount from about 2% to about 90% w/w, and a chelating agent in an amount from about 0.0001% to 0.05% w/w.

In a preferred embodiment, the present invention is directed to liquid spray formulations comprising naloxone, a pharmaceutically acceptable salt or a derivative thereof, in an amount from about 1% to about 20% w/w, water in an amount from about 30% to about 99% w/w, a co-solvent in an amount from about 2% to about 90% w/w, and a chelating agent in an amount from about 0.0005% to 0.05% w/w.

In a preferred embodiment, the liquid spray formulations of the present invention further comprise a permeation enhancer selected from the group consisting of menthol in an amount from about 0.001% to about 10.0% w/w, caprylic acid in an amount from about 0.1% to 10% w/w, benzalkonium chloride ("BKC") in an amount from about 0.001% to 10% w/w and a combination thereof.

In another preferred embodiment, the formulation contains edetate disodium dihydrate as the chelating agent at 0.001% w/w or 0.05% w/w.

In yet another embodiment, the present invention is directed to naloxone, a pharmaceutically acceptable salt or a derivative thereof, in an amount from about 1% to about 16% w/w, water in an amount from about 20% to about 85% w/w, a co-solvent in an amount from about 5% to about 55% w/w, and a chelating agent in an amount from about 0.0001% to 0.05%. In a preferred embodiment of the formulation, naloxone is a salt. In yet another preferred embodiment, the formulation further comprises a permeation enhancer selected from menthol in an amount from about 0.01% to about 10% w/w, caprylic acid in an amount from about 0.1% to 10% w/w, BKC in an amount from about 0.001% to 10% w/w, and a combination thereof.

In another preferred embodiment, the chelating agent is edetate disodium dihydrate, preferably at a concentration from about 0.001% to about 0.5% w/w.

In yet another embodiment, the present invention is directed to naloxone, a pharmaceutically acceptable salt or a derivative thereof, in an amount from about 1% to about 10% w/w, water in an amount from about 30% to about 85% w/w, a co-solvent in an amount from about 7% to about 55% w/w, and a chelating agent in an amount from about 0.0001% to 0.05%, In a preferred embodiment of the formulation, naloxone is a salt. In another preferred embodiment, the formulation further comprises a preservative, preferably from about 0.01% to about 0.5% w/w. In a more preferred embodiment the chelating agent is edetate disodium dihydrate. In another preferred embodiment, the preservative is methyl paraben.

In another embodiment, formulations of the present invention do not contain a preservative.

In a further embodiment, the present invention is directed to naloxone, a pharmaceutically acceptable salt or a derivative thereof in an amount from about 1% to about 10% w/w, water in an amount from about 35% to about 85% w/w, a co-solvent in an amount from about 7% to about 55% w/w, and a chelating agent in an amount from about 0.001% to about 0.02% w/w. In a preferred embodiment of this formulation, naloxone is a salt. In another preferred embodiment, the formulation also contains a preservative in an amount from about 0.05% to about 0.2% w/w. In yet another preferred embodiment, the formulation contains edetate disodium dihydrate as the chelating agent.

In a further embodiment, the present invention is directed to liquid spray formulations comprising naloxone hydrochloride dihydrate from about 1% to about 10% w/w, water from about 35% to about 84% w/w, ethanol from about 2% to about 50% w/w, EDTA from about 0.001% to about 0.02% w/w and optionally propylene glycol from about 5% to about 10% w/w and optionally, methyl paraben at about 0.1% w/w.

In another embodiment, the liquid spray formulations of the present invention do not contain an isotonicity agent.

In another embodiment, the liquid spray formulations of the present invention do not contain sodium chloride.

In another embodiment, the liquid spray formulations of the present invention do not contain benzalkonium chloride.

In another embodiment, the liquid spray formulations of the present invention do not contain a buffer.

In another embodiment, the liquid spray formulations of the present invention do not contain citric acid.

In some embodiments, the formulations of the present invention contain citric acid or sodium hydroxide or hydrochloric acid solution as a pH adjustor.

Pharmaceutically acceptable salts that can be used in accordance with the current invention include but are not limited to hydrochloride, hydrochloride dihydrate, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts.

In preferred embodiments, the pharmaceutically acceptable salt is hydrochloride.

Derivatives of naloxone that can be used in accordance with the current invention include but are not limited to 3-O-acyl, phenylhydrazone, and methiodide derivatives.

The solvent used with the present invention is United States Pharmacopeia ("USP") purified water.

Co-solvents that can be used in accordance with the current invention are alcohols, and glycols or a mixture thereof.

Alcohols that can be used in accordance with the current invention include but are not limited to methanol, ethanol (also known as dehydrated alcohol), propyl alcohol, butyl alcohol and the like, but do not include benzyl alcohol.

In formulations of the current invention that do not contain an alcohol, the term "alcohol" includes all alcohols including benzyl alcohol.

Glycols that can be used in accordance with the current invention include but are not limited to propylene glycol, polypropylene glycol, and butylene glycol and polyethylene glycols such as PEG 200, PEG 300, PEG 400 and PEG 600 and the like.

In preferred embodiments, the co-solvent is ethanol or propylene glycol or a mixture thereof.

In another preferred embodiment, the amount of co-solvent included in the formulation is from about 2% to about 90% w/w. In other more preferred embodiments, the amount of co-solvent included in the formulation is about 5% or about 10% w/w propylene glycol. In other more preferred embodiments, the amount of co-solvent included in the formulation is about 2%, about 10%, about 20% or about 50% w/w ethanol.

In other more preferred embodiments the co-solvent is a mixture of propylene glycol at about 5% w/w and ethanol at about 50% w/w, or a mixture of propylene glycol at about 5% w/w and ethanol at about 20% w/w, or a mixture of propylene glycol at about 10% w/w and ethanol at about 10% w/w, or propylene glycol at about 10% w/w and ethanol at about 2% w/w or 10% w/w ethanol.

Solubilizers that can be used in accordance with the current invention are hydroxypropyl beta-cyclodextrin ("HPβCD") and sulfobutylether cyclodextrin or a mixture thereof.

In preferred embodiments, the solubilizer is HPβCD.

In more preferred embodiments the amount of HPβCD is about 30% w/w.

Permeation enhancers that can be used in accordance with the current invention include but are not limited to menthol, limonene, carvone, methyl chitosan, polysorbates including Tween® 80 (polysorbate 80; Tween is a registered trademark of Uniqema Americas, LLC), sodium lauryl sulfate, glyceryl oleate, caprylic acid, pelargonic acid, capric acid, undecylenic acid, lauric acid, myristic acid, palmitic acid, oleic acid, stearic acid, linolenic acid, arachidonic acid, benzalkonium chloride (BKC), cetylpyridium chloride, edetate disodium dihydrate, sodium desoxycholate, sodium deoxyglycolate, sodium glycocholate, sodium caprate, sodium taurocholate, sodium hydroxybenzoyal amino caprylate, dodecyl dimethyl aminopropionate, L-lysine, glycerol oleate, glyceryl monostearate, citric acid, and peppermint oil. Preferably the permeation enhancer is selected from the group consisting of menthol, benzalkonium chloride, edetate disodium dihydrate, caprylic acid, and a combination thereof.

In preferred embodiments, the amount of permeation enhancer is from about 0.001% to about 10% w/w. In a more preferred embodiment, the formulations contain from about 0.01% to about 5.0% w/w permeation enhancer. In a preferred embodiment, the formulations contain from about 0.02% to about 2.0% w/w permeation enhancer. In a most preferred embodiment, the formulations contain 2.0% w/w permeation enhancer.

In preferred embodiment, the permeation enhancer is L-menthol, caprylic acid, BKC, edetate disodium dihydrate (EDTA) or combination thereof, the preferred amount of L-menthol is from about 0.001% to about 10.0% w/w, caprylic acid is from about 0.1% to about 10% w/w, BKC is from about 0.001 to about 10% w/w, and EDTA is from about 0.0005% to 0.1% w/w. In a more preferred embodiment, the formulations contain from about 0.01% to about 0.5% w/w L-menthol, about 0.5% to about 5% w/w caprylic acid, about 0.005 to about 0.1% w/w BKC, about 0.005% to about 0.05% w/w EDTA, or a combination thereof. In an even more preferred embodiment, the formulations contain from about 0.02% to about 0.5% w/w L-menthol, about 1% to about 2% w/w caprylic acid, about 0.01 to about 0.1% w/w BKC, about 0.005 to about 0.05 w/w EDTA or a combination thereof. In a most preferred embodiment, the formulations contain about 0.5% w/w L-menthol, about 2% w/w caprylic acid, about 0.01% w/w BKC, about 0.005% edetate disodium dihydrate, or a combination thereof.

In yet another embodiment, the permeation enhancer is about 0.5% w/w of menthol.

In yet another preferred embodiment, the permeation enhancer is about 2.0% w/w caprylic acid.

In a most preferred embodiment, the permeation enhancer is about 0.01% w/w of benzalkonium chloride (BKC).

In a most preferred embodiment, the permeation enhancer is about 0.005%, 0.01%, 0.015% or 0.02% w/w of edetate disodium dihydrate (EDTA).

In a further most preferred embodiment, the permeation enhancer is a combination of 2.0% w/w caprylic acid and 0.01% w/w of benzalkonium chloride.

Formulations of the present invention may have a pH range from about 2.0 to about 7.0, preferably from about 3 to about 6 and more preferably from about 3 to about 4.5 pH, most preferably 3 or 4.5±01, pH adjustors that can be used in accordance with the present invention include but are not limited to citric acid and sodium hydroxide. In preferred embodiments, the amount of sodium hydroxide or citric acid is from about 0.002% to about 0.03% w/w. In more preferred embodiments, the amount of sodium hydroxide is about 0.015% w/w. In other more preferred embodiments, the amount of sodium hydroxide is about 0.012% w/w.

In a further embodiment, the formulation contains a permeation enhancer, a sweetener, a sweetness enhancer, a pH modifier, a flavoring agent, a preservative, or a combination thereof.

In a preferred embodiment, the formulations contain a sweetener. In a more preferred embodiment, the sweetener is selected from the group consisting of sucralose, aspartame, saccharin, dextrose, mannitol, glycerin, and xylitol. In a preferred embodiment, the formulations contain from about 0.001% w/w to about 2% w/w of sweetener. In a more preferred embodiment, the formulations contain from about 0.05% w/w to about 1% w/w of the sweetener. In a most preferred embodiment, the formulations contain sucralose as sweetener at about 0.8% w/w.

In another embodiment, the formulations contain a flavoring agent. In a preferred embodiment, the formulations contain a flavoring agent selected from the group consisting of peppermint oil, menthol, spearmint oil, citrus oil, cinnamon oil, strawberry flavor, cherry flavor, raspberry flavor, orange oil, and a combination thereof. Other appropriate flavoring agents known by those of skill in art could also be added to formulations of the present invention. In a preferred embodiment, the formulations contain from about 0.001% w/w to about 1% w/w of the flavoring agent. In a more preferred embodiment, the formulations contain from about 0.005% w/w to about 0.5% w/w of the flavoring agent. In a most preferred embodiment, the formulations contain strawberry as flavoring agent at about 0.08% w/w.

In yet another embodiment, the formulations of the present invention are capable of producing a droplet size distribution wherein the mean Dv(10) is from about 11 to about 35 microns during administration.

In a further embodiment, the formulations of the present invention are capable of producing a droplet size distribution wherein the mean Dv(50) is from about 25 to about 55 microns during administration.

In yet another embodiment, the formulations of the present invention are capable of producing a droplet size distribution wherein the mean Dv(90) is from about 75 to about 600 microns during administration. Preferably, the formulations of the present invention are capable of producing a droplet size distribution wherein the mean Dv(90) is from about 85 to about 600 microns during administration.

Formulations without an Alcohol

In a further embodiment, the invention is directed to stable liquid spray formulations comprising an effective amount of naloxone, a pharmaceutically acceptable salt or a derivative thereof, water, a chelating agent and optionally, a co-solvent and the formulations do not contain an alcohol.

In a further embodiment, the invention is directed to stable liquid spray formulations comprising an effective amount of naloxone, a pharmaceutically acceptable salt or a derivative thereof, water, and a permeation enhancer or a chelating agent, and optionally, a co-solvent and the formulations do not contain an alcohol.

In another embodiment, the stable liquid spray formulations of the present invention contain a preservative, preferably from about 0.01% to about 0.5% w/w. In a more preferred embodiment, the preservative is methyl paraben.

In another embodiment, the stable liquid spray formulations of the present invention do not contain a preservative.

In another embodiment, the stable liquid spray formulations of the present invention are suitable for nasal administration.

In another embodiment, the liquid spray formulations of the present invention do not contain an isotonicity agent.

In another embodiment, the liquid spray formulations of the present invention do not contain sodium chloride.

In another embodiment, the liquid spray formulations of the present invention do not contain benzalkonium chloride.

In another embodiment, the liquid spray formulations of the present invention do not contain a buffer.

In another embodiment, the liquid spray formulations of the present invention do not contain citric acid.

In a preferred embodiment, the liquid spray formulation comprises from about 0.01% w/w to about 20% w/w naloxone or a salt or derivative thereof. In a more preferred embodiment, the liquid spray formulation comprises from about 1% w/w to about 12% w/w naloxone or a salt or derivative thereof. In an even more preferred embodiment, the formulations contain from about 2% w/w to about 10% w/w naloxone or a salt or derivative thereof.

In another embodiment, the formulations contain from about 20% w/w to about 99% water. In a preferred embodiment, the formulations contain from about 30% w/w to about 98% w/w water. In a more preferred embodiment, the formulations contain from about 80% w/w to about 98% w/w water. In a most preferred embodiment, the formulations contain from about 81% w/w to about 98% w/w water. Aqueous formulations of the present invention preferably contain from about 70% to about 99% w/w water, more preferably, from about 80% to about 99% w/w water. In most preferred embodiments, aqueous formulations contain about from about 84% to about 98% w/w water.

In an embodiment, the formulations contain from about 5% w/w to about 50% w/w glycerol. In a preferred embodiment, the formulations contain from about 10% w/w to about 40% w/w glycerol. In a more preferred embodiment, the formulations contain from about 15% w/w to about 35% w/w glycerol.

In another embodiment, the formulations may contain from about 0.1% w/w to about 50% w/w polyethylene glycol 400. In a more preferred embodiment, the formulations contain from about 10% w/w to about 40% w/w polyethylene glycol 400.

In another embodiment, the formulations contain from about 0.1% w/w to about 50% w/w propylene glycol. In a more preferred embodiment, the formulations contain from about 10% w/w to about 40% w/w propylene glycol. In an even more preferred embodiment, the present invention contains from about 5% to about 10% w/w propylene glycol.

In another embodiment, the formulation contains a pharmaceutically acceptable salt of naloxone. In a preferred embodiment, the formulation contains a salt selected from the group consisting of hydrochloride, citrate, halide, phosphate, sulfate, acetate, ascorbate, maleate, succinate, carbonate, mesylate and lactate. One of skill in the art could use other pharmaceutically acceptable naloxone salts in the formulations of the present invention.

In a preferred embodiment, the antioxidant is selected from the group consisting of ascorbic acid, cysteine HCl monohydrate, citric acid, ethylenediamine tetra acetic acid (EDTA), methionine, sodium citrate, sodium ascorbate, sodium thiosulfate, sodium metabisulfite, sodium bisulfite, glutathione and thioglycerol. Other appropriate antioxidants known by those of skill in the art could also be added to formulations of the present invention.

In a preferred embodiment, the formulations contain from about 0.0001% w/w to about 0.5% w/w of the antioxidant. In a more preferred embodiment, the formulations may contain from about 0.005% w/w to about 0.2% w/w of the antioxidant. In a most preferred embodiment, the formulations contain 0.05% w/w or 0.02% w/w of the antioxidant.

In another embodiment, the formulations of the present invention contain a chelating agent. In a preferred embodiment, the chelating agent is edetate disodium dihydrate In an embodiment, the formulations contain from about 0.0001% to about 0.5% w/w of the chelating agent. In a preferred embodiment, the formulations contain from about 0.001% to about 0.50% w/w of the chelating agent. In a more preferred embodiment, the formulations contain from about 0.005% to about 0.05% w/w of the chelating agent.

In a further embodiment, the formulation contains a permeation enhancer, a sweetener, a sweetness enhancer, a pH modifier, a flavoring agent, a preservative, or a combination thereof.

In another embodiment, the formulation contains a permeation enhancer. In a preferred embodiment, the permeation enhancer is selected from the group consisting of menthol, limonene, carvone, methyl chitosan, caprylic acid pelargonic acid, capric acid, undecylenic acid, lauric acid, myristic acid, palmitic acid, oleic acid, stearic acid, linolenic acid, arachidonic acid, polysorbates including Tween® 80, sodium edetate, benzalkonium chloride (BKC), cetylpyridinium chloride, sodium lauryl sulfate, citric acid, sodium desoxycholate, sodium deoxyglycolate, glyceryl oleate, glyceryl monostearate, Sodium hydroxybenzoyal amino caprylate, sodium caprate, dodecyl dimethyl aminopropionate, L-lysine, sodium glycocholate, citric acid, peppermint oil and a combination thereof. In a more preferred embodiment, the permeation enhancer is selected from the group consisting of polysorbates including Tween® 80, sodium edetate, benzalkonium chloride (BKC), cetylpyridinium chloride, sodium lauryl sulfate, citric acid, sodium desoxycholate, sodium deoxyglycolate, glyceryl oleate, glyceryl monostearate, L-lysine, sodium glycocholate, sodium taurocholate, citric acid, and a combination thereof. In an even more preferred embodiment, the permeation enhancer is selected from the group consisting of menthol, caprylic acid and BKC.

In preferred embodiments, the amount of permeation enhancer is from about 0.001% to about 10% w/w. In a more preferred embodiment, the formulations contain from about 0.001% to about 2.5% w/w permeation enhancer. In a most preferred embodiment, the formulations contain from about 0.02% to about 2.0% w/w permeation enhancer.

In a preferred embodiment, the permeation enhancer is menthol, caprylic acid, BKC or a combination thereof, the preferred amount of L-menthol is from about 0.001% to about 10% w/w, caprylic acid is from about 0.1% to 10% w/w, BKC is from about 0.001 to 10% w/w. In a more preferred embodiment, the formulations contain from about 0.01% to about 0.5% w/w L-menthol, about 0.5% to 5% w/w caprylic acid, about 0.005 to 0.1% w/w BKC. In an even more preferred embodiment, the formulations contain from about 0.02% to about 0.5% w/w L-menthol, about 1% to 2% w/w caprylic acid, about 0.01 to 0.1% w/w BKC. In a most preferred embodiment, the formulations contain about 0.5% w/w L-menthol, about 2% w/w caprylic acid and about 0.005 w/w BKC.

In yet another embodiment, the permeation enhancer is about 0.5% w/w of menthol.

In yet another preferred embodiment, the permeation enhancer is about 2.0% w/w caprylic acid.

In a most preferred embodiment, the permeation enhancer is about 0.01% w/w of benzalkonium chloride (BKC).

In a preferred embodiment, the formulations contain a sweetener. In a more preferred embodiment, the sweetener is selected from the group consisting of sucralose, aspartame, saccharin, dextrose, mannitol, glycerin, and xylitol. In a preferred embodiment, the formulations contain from about 0.001% w/w to about 2% w/w of sweetener. In a more preferred embodiment, the formulations contain from about 0.05% w/w to about 1% w/w of the sweetener. In a most preferred embodiment, the formulations contain sucralose as a sweetener at about 0.8% w/w.

In a further embodiment, the formulation may contain a sweetness enhancer, an ammonium salt form of crude and refined Glycyrrhizic Acid, for example, Magnasweet® product (available from Mafco Worldwide Corporation, Magnasweet is a registered trademark of Mafco Worldwide Corporation). Magnasweet® products use the ammonium salt forms of crude and refined Glycyrrhizic Acid. Glycyrrhizic Acid is also available as a pure derivative in the sodium and potassium salt forms.

In another embodiment, the formulations contain a pH modifier. In a preferred embodiment, the pH modifier adjusts the pH of the formulation to from about 2 to about 7. In a more preferred embodiment, the pH modifier adjusts the pH of the formulation to from about 3 to about 6, from about 4 to about 5 or from about 2 to about 4. In most preferred embodiments, the pH modifier adjusts the pH of the formulations to about 2.5, or 3, or 4.5±0.1.

In another embodiment, the formulations contain a flavoring agent. In a preferred embodiment, the formulations contain a flavoring agent selected from the group consisting of peppermint oil, menthol, spearmint oil, citrus oil, cinnamon oil, strawberry flavor, cherry flavor, raspberry flavor, orange oil, and a combination thereof. Other appropriate flavoring agents known by those of skill in the art could also be added to formulations of the present invention. In a preferred embodiment, the formulations contain from about 0.001% w/w to about 1% w/w of the flavoring agent. In a more preferred embodiment, the formulations contain from about 0.005% w/w to about 0.5% w/w of the flavoring agent. In a most preferred embodiment, the formulations contain strawberry as the flavoring agent at about 0.08% w/w.

In yet another embodiment, the formulations may contain a preservative. In a preferred embodiment, the preservative is selected from the group consisting of butyl paraben, methyl paraben, ethyl paraben, propyl paraben, sodium benzoate, and benzoic acid. In a preferred embodiment, the formulations contain from about 0.001% w/w to about 1% w/w of the preservative. In a more preferred embodiment, the formulations contain from about 0.005% w/w to about 0.2% w/w of the preservative. In a most preferred embodiment, the formulations contain methyl paraben as a preservative at about 0.1% w/w.

In a further embodiment, the invention is directed to stable liquid spray formulations comprising from about 1% to about 16% w/w naloxone, a pharmaceutically acceptable salt or a derivative thereof, about 10% to about 98% w/w water, about 0.005% to about 0.05% w/w of a chelating agent, preferably edetate disodium dihydrate and optionally, about 2% to about 90% w/w of a co-solvent, preferably propylene glycol and the formulations do not contain an alcohol.

In a further embodiment, the invention is directed to stable liquid spray formulations comprising from about 1% to about 16% w/w naloxone, a pharmaceutically acceptable salt or a derivative thereof, about 30% to about 98% w/w water, about 0.005% to about 0.05% w/w of a chelating agent, preferably edetate disodium dihydrate and optionally, about 5% to about 55% w/w of a co-solvent, preferably propylene glycol and the formulations do not contain an alcohol.

In a further embodiment, the invention is directed to stable liquid spray formulations comprising from about 1% to about 10% w/w naloxone, a pharmaceutically acceptable salt or a derivative thereof, about 80% to about 98% w/w water, about 0.005% to about 0.05% w/w of a chelating agent, preferably edetate disodium dihydrate and optionally, about 5% to about 10% w/w of a co-solvent, preferably propylene glycol, and optionally about 0.1% w/w of a preservative, preferably methyl paraben and the formulations do not contain an alcohol.

In yet another embodiment, the formulations of the present invention are capable of producing a droplet size distribution wherein the mean $Dv(10)$ is from about 12 to about 20 microns during administration.

In a further embodiment, the formulations of the present invention are capable of producing a droplet size distribution wherein the mean $Dv(50)$ is from about 25 to about 35 microns during administration.

In yet another embodiment, the formulations of the present invention are capable of producing a droplet size distribution wherein the mean $Dv(90)$ is from about 40 to about 150 microns during administration. Preferably, the formulations of the present invention are capable of producing a droplet size distribution wherein the mean $Dv(90)$ is from about 60 to about 110 microns during administration.

All claims, aspects and embodiments of the invention, and specific examples thereof, are intended to encompass equivalents thereof.

In a further embodiment, the invention is directed to treating patients by administering the formulations (with or without an alcohol) of the present invention to the patient. In a preferred embodiment, the formulations are administered in order to treat opioid overdose, opioid dependence, and/or congenital insensitivity to pain with anhidrosis.

Definitions

As used herein, all numerical values relating to amounts, weights, and the like, that are defined as "about" each particular value is plus or minus 10%. For example, the phrase "about 10% w/w" is to be understood as "9% to 11% w/w." Therefore, amounts within 10% of the claimed value are encompassed by the scope of the claims.

As used herein "% w/w" refers to the percent weight of the total formulation.

As used herein the term "effective amount" refers to the amount necessary to treat a patient in need thereof.

As used herein the term "patient" refers but is not limited to a person that is being treated for opioid dependence, opioid overdose, insensitivity to pain with anhidrosis, or another affliction or disease that can be treated with naloxone.

As used herein the phrase "pharmaceutically acceptable" refers to ingredients that are not biologically or otherwise undesirable in a sublingual or intranasal dosage form.

As used herein, "stable" refers to formulations which maintain greater than 95% purity following at least four weeks at about 40° C.

Preferably, the (alcohol and alcohol-free) formulations of the present invention are propellant free. As used herein, "propellant free" refers to a formulation that is not administered using compressed gas.

As used herein, the term "isotonicity agent" refers to any compound used to alter or regulate the osmotic pressure of a formulation.

As used herein, the term "buffer" refers to any compound used to maintain the pH of a formulation.

The following examples are intended to illustrate the present invention and to teach one of ordinary skill in the art how to make and use the invention. They are not intended to be limiting in any way.

EXAMPLES

Example 1: Preparation of Naloxone Formulations Containing Ethanol

Liquid spray formulations were created by first degassing ethanol and USP purified water, separately. Next, the ethanol and purified water were each purged with nitrogen. Soluble excipients were then dissolved in either the ethanol or the purified water based on their solubility. Next, the solutions were combined. Naloxone was added to the final solution and mixed until dissolved.

Strawberry flavor was used as the source of the flavoring agent.

TABLE 1

Stable Liquid Naloxone Spray Formulations

| Formulation | Control | #1A | #2A | #3A | #4A | #5A | #6A | #7A |
|---|---|---|---|---|---|---|---|---|
| Naloxone Hydrochloride Dihydrate | 2.44 | 2.44 | 2.44 | 2.44 | 2.44 | 4.00 | 6.7 | 10.1 |
| Water (USP) | 37.56 | 37.55 | 37.55 | 37.54 | 37.54 | 34.45 | 33.23 | 29.83 |
| Ethanol | 55 | 55 | 55 | 55 | 55 | 55 | 55 | 55 |
| Propylene Glycol | 5 | 5 | 5 | 5 | 5 | 5 | 5 | 5 |
| L-menthol | | | | | | 0.05 | | |
| Sodium Thiosulfate | | 0.01 | 0.01 | | | | | |
| Citric Acid | | 0.0025 | | | | | | |
| Flavoring agent | | | | | | 0.08 | | |
| Edetate disodium dihydrate | | | 0.005 | 0.005 | 0.005 | 0.005 | 0.005 | 0.005 |
| BHA | | | | 0.01 | | | | |
| BHT | | | | 0.005 | | | | |
| Sodium Ascorbate | | | | | 0.02 | 0.02 | 0.02 | 0.02 | values = % w/w

Example 2: Stability Testing of Naloxone Formulations

The formulations listed in Table 1 were subjected to stability testing at 40° C. and 55° C.±2° C. under 75%±5% relative humidity for eight weeks. The stability data was collected at zero, one, two, three, four, and eight weeks at 55° C. and at zero, four, and eight weeks at 40° C. Assay and impurities were detected using high performance liquid chromatography with an ultraviolet detector. The assay was performed at 288 nm and indicated as a % of initial concentration. For all impurities, analysis was performed at 240 nm and expressed as a % area. Amounts of particular impurities are listed in Tables 2A to 2F and 3A to 3H as a percentage of the area of each formulation along with amount of total impurities. "BQL" refers to "Below Quantifiable Limit" and "ND" refers to "Not Detected."

Tables 2A to 2F. Stability Data for Liquid Naloxone Spray Formulations Stored at 40° C.±2° C. Under 75%±5% Relative Humidity 2A. Stabiity of Control Stored at 40° C.

| Naloxone | RRT | T = 0 | 4 Weeks | 8 Weeks |
|---|---|---|---|---|
| Impurity C | 0.66 | ND | 0.81% | 0.92% |
| Impurity A | 0.83 | ND | 0.37% | 0.51% |
| Impurity F | 0.93 | ND | ND | ND |
| Impurity D | 1.14 | ND | ND | ND |
| Impurity E | 2.85 | ND | 5.59% | 5.53% |
| Impurity B | 3.21 | ND | ND | ND |
| Unknown | 0.30 | ND | 0.13% | 0.18% |
| Impurities | 0.50 | ND | 0.28% | 0.46% |
| Total Impurities | | 0.00% | 7.18% | 7.60% |

2B. Stability of Form. #1A (with Sod. Thiosulphate & Citric Acid) Stored at 40° C.

| Naloxone | RRT | T = 0 | 4 Weeks | 8 Weeks |
|---|---|---|---|---|
| Impurity C | 0.66 | ND | BQL | BQL |
| Impurity A | 0.83 | ND | BQL | BQL |
| Impurity F | 0.93 | ND | ND | ND |
| Impurity D | 1.14 | ND | ND | ND |
| Impurity E | 2.85 | ND | ND | ND |
| Impurity B | 3.21 | ND | ND | ND |
| Total Impurities | | 0.00% | 0.00% | 0.00% |

2C. Stability of Form. #2A (with Sod. Thiosulphate & Edetate Disodium Dihydrate) Stored at 40° C.

| Naloxone | RRT | T = 0 | 4 Weeks | 8 Weeks |
|---|---|---|---|---|
| Impurity C | 0.66 | ND | BQL | BQL |
| Impurity A | 0.83 | ND | BQL | BQL |
| Impurity F | 0.93 | ND | ND | ND |
| Impurity D | 1.14 | ND | ND | ND |
| Impurity E | 2.85 | ND | ND | ND |
| Impurity B | 3.21 | ND | ND | ND |
| Total Impurities | | 0.00% | 0.00% | 0.00% |

2D. Stability of Form. #3A (with BHA & BHT) Stored at 40° C.

| Naloxone | RRT | T = 0 | 4 Weeks | 8 Weeks |
|---|---|---|---|---|
| Impurity C | 0.66 | ND | BQL | BQL |
| Impurity A | 0.83 | ND | BQL | BQL |
| Impurity F | 0.93 | ND | ND | ND |
| Impurity D | 1.14 | ND | ND | ND |
| Impurity E | 2.85 | ND | ND | ND |
| Impurity B | 3.21 | ND | ND | ND |
| Total Impurities | | 0.00% | 0.00% | 0.00% |

2E. Stability of Form. #4A (with Sod. Ascorbate and Edetate Disodium Dihydrate) Stored at 40° C.

| Naloxone | RRT | T = 0 | 4 Weeks | 8 Weeks |
|---|---|---|---|---|
| Impurity C | 0.66 | ND | BQL | BQL |
| Impurity A | 0.83 | ND | 0.15% | 0.19% |
| Impurity F | 0.93 | ND | ND | ND |
| Impurity D | 1.14 | ND | ND | ND |
| Impurity E | 2.85 | ND | ND | ND |
| Impurity B | 3.21 | ND | ND | ND |
| Total Impurities | | 0.00% | 0.15% | 0.19% |

2F. Stability of Form. #5A (with Sod. Ascorbate and Edetate Disodium Dihydrate) Stored at 40° C.

| Naloxone | RRT | T = 0 | 4 Weeks | 3 Months |
|---|---|---|---|---|
| Assay (%) | | 100 | 97.77 | 97.6 |
| Impurity C | 0.66 | ND | ND | 0.03 |
| Impurity A | 0.83 | 0.11 | 0.12 | 0.15 |
| Impurity F | 0.93 | ND | ND | ND |
| Impurity D | 1.14 | ND | ND | ND |
| Impurity E | 2.85 | ND | 0.13 | 0.13 |
| Impurity B | 3.21 | ND | ND | ND |
| Total Impurities | | 0.11% | 0.25% | 0.29% |

Liquid naloxone formulations of the present invention contained less than one percent total impurities after eight weeks at 40° C. This is a stark contrast to the control formulation which contained 7.6% impurities at the same time. Specifically, the formulations which contained sodium thiosulfate or BHA and BHT resulted in 0% detected impurities after eight weeks. Also, formulations which contain sodium ascorbate (0.02% wt/wt) and edetate disodium dihydrate (0.005% wt/wt) resulted in only 0.29% total impurities after 3 months.

Tables 3A to 3H. Stability Data for Liquid Naloxone Spray Formulations Stored at 55° C.±2° C.

3A. Stability of Control Stored at 55° C.

| Naloxone | RRT | T = 0 | 1 Week | 2 Weeks | 3 Weeks | 4 Weeks | 8 Weeks |
|---|---|---|---|---|---|---|---|
| Impurity C | 0.66 | ND | ND | ND | 0.54% | 0.33% | 0.35% |
| Impurity A | 0.83 | ND | ND | ND | 1.31% | 1.39% | 1.59% |
| Impurity F | 0.93 | ND | ND | ND | ND | ND | ND |
| Impurity D | 1.14 | ND | ND | ND | ND | ND | ND |
| Impurity E | 2.85 | ND | ND | ND | ND | ND | ND |
| Impurity B | 3.21 | ND | ND | ND | ND | ND | ND |
| Unknown | 0.30 | — | — | — | — | 0.1% | 0.32% |
| Impurities | 0.35 | — | — | — | 0.15% | 0.16% | 0.08% |
| | 0.50 | — | — | — | 0.83% | 0.81% | 0.67% |
| | 2.85 | — | — | — | 4% | 7.50% | 6.65% |
| Total Impurities | | 0.00% | 0.00% | 0.00% | 6.83% | 10.29% | 9.66% |

3B. Stability of Form. #1A (with Sod. Thiosulphate & Citric AcId) Stored at 55° C.

| Naloxone | RRT | T = 0 | 1 Week | 2 Weeks | 3 Weeks | 4 Weeks | 8 Weeks |
|---|---|---|---|---|---|---|---|
| Impurity C | 0.66 | ND | ND | ND | 0.12% | 0.37% | 0.29% |
| Impurity A | 0.83 | ND | ND | ND | 0.14% | 0.67% | 1.01% |
| Impurity F | 0.93 | ND | ND | ND | ND | ND | ND |
| Impurity D | 1.14 | ND | ND | ND | ND | ND | ND |
| Impurity E | 2.85 | ND | ND | ND | 0.55% | 1.88% | 1.52% |
| Impurity B | 3.21 | ND | ND | ND | ND | ND | ND |
| Unknown | 0.32 | — | — | — | — | 0.09% | 0.25% |
| Impurities | 0.52 | — | — | — | 0.06% | 0.51% | 0.59% |
| Total Impurities | | 0.00% | 0.00% | 0.00% | 0.87% | 3.52% | 3.66% |

3C. Stability of Form. #2A (with Sod. Thiosulphate & Edetate Disodium Dihydrate) Stored at 55° C.

| Naloxone | RRT | T = 0 | 1 Week | 2 Weeks | 3 Weeks | 4 Weeks | 8 Weeks |
|---|---|---|---|---|---|---|---|
| Impurity C | 0.66 | ND | ND | ND | ND | BQL | BQL |
| Impurity A | 0.83 | ND | ND | ND | BQL | 0.07% | 0.11% |
| Impurity F | 0.93 | ND | ND | ND | ND | ND | ND |
| Impurity D | 1.14 | ND | ND | ND | ND | ND | ND |
| Impurity E | 2.85 | ND | ND | ND | ND | ND | ND |
| Impurity B | 3.21 | ND | ND | ND | ND | ND | ND |
| Unknown Impurities | 0.52 | — | — | — | — | — | 0.08% |
| Total Impurities | | 0.00% | 0.00% | 0.00% | 0.00% | 0.07% | 0.19% |

3D. Stability of Form. #3A (with BHA & BHT) Stored at 55° C.

| Naloxone | RRT | T = 0 | 1 Week | 2 Weeks | 3 Weeks | 4 Weeks | 8 Weeks |
|---|---|---|---|---|---|---|---|
| Impurity C | 0.66 | ND | ND | ND | ND | ND | BQL |
| Impurity A | 0.83 | ND | ND | ND | BQL | 0.07% | 0.13% |
| Impurity F | 0.93 | ND | ND | ND | ND | ND | ND |
| Impurity D | 1.14 | ND | ND | ND | ND | ND | ND |
| Impurity E | 2.85 | ND | ND | ND | ND | ND | ND |
| Impurity B | 3.21 | ND | ND | ND | ND | ND | ND |
| Unknown Impurities | 0.50 | — | — | — | — | — | 0.08% |
| Total impurities | | 0.00% | 0.00% | 0.00% | 0.00% | 0.07% | 0.21% |

3E. Stability of Form. #4A (with Sod. Ascorbate and Edetate Disodium Dihydrate) Stored at 55° C.

| Naloxone | RRT | T = 0 | 1 Week | 2 Weeks | 3 Weeks | 4 Weeks | 8 Weeks |
|---|---|---|---|---|---|---|---|
| Impurity C | 0.66 | ND | ND | ND | ND | ND | 0.06% |
| Impurity A | 0.83 | ND | ND | ND | 0.11% | 0.19% | 0.19% |
| Impurity F | 0.93 | ND | ND | ND | ND | ND | ND |
| Impurity D | 1.14 | ND | ND | ND | ND | ND | ND |
| Impurity E | 2.85 | ND | ND | ND | ND | ND | ND |
| Impurity B | 3.21 | ND | ND | ND | ND | ND | ND |
| Total Impurities | | 0.00% | 0.00% | 0.00% | 0.11% | 0.19% | 0.25% |

3F. Stability of Form. #5A (with Sod. Ascorbate and Edetate Disodium Dihydrate) Stored at 55° C.

| Naloxone | RRT | T = 0 | 2 Weeks | 4 Weeks | 6 Weeks | 8 Weeks |
|---|---|---|---|---|---|---|
| Assay (%) | | 100 | 102.37 | 98.75 | 98.51 | 100.76 |
| Impurity C | 0.66 | ND | ND | ND | ND | 0.05% |
| Impurity A | 0.83 | 0.11 | 0.14 | 0.15 | 0.19 | 0.17% |
| Impurity F | 0.93 | ND | ND | ND | ND | ND |
| Impurity D | 1.14 | ND | ND | ND | ND | ND |
| Impurity E | 2.85 | ND | 0.13 | 0.11 | 0.12 | 0.12% |
| Impurity B | 3.21 | ND | ND | ND | ND | ND |
| Unknown Impurities | 0.49 | — | — | — | 0.06% | 0.05% |
| | 0.79 | — | — | — | 0.03% | — |
| | 3.90 | — | — | 0.05% | 0.07% | 0.05% |
| Total Impurities | | 0.11% | 0.27% | 0.31% | 0.47% | 0.44% |

3H. Stability of Form. #6A (with Sod. Ascorbate and Edetate Disodium Dihydrate) Stored at 55° C.

| Naloxone | RRT | T = 0 | 2 Weeks | 4 Weeks | 8 Weeks |
|---|---|---|---|---|---|
| Assay (%) | | 100.00 | 101.35 | 102.69 | 102.99 |
| Impurity C | 0.66 | ND | BQL | BQL | 0.08% |
| Impurity A | 0.81 | BQL | 0.08% | 0.19% | 0.18% |
| Impurity F | 0.93 | ND | ND | ND | ND |

3H. Stability of Form. #6A (with Sod. Ascorbate and Edetate Disodium Dihydrate) Stored at 55° C.

| Naloxone | RRT | T = 0 | 2 Weeks | 4 Weeks | 8 Weeks |
|---|---|---|---|---|---|
| Impurity D | 1.14 | ND | ND | ND | ND |
| Impurity E | 2.85 | 0.04% | 0.07% | 0.06% | 0.10% |
| Impurity B | 3.21 | ND | ND | ND | 0.12% |
| Unknown Impurities | 0.50 | — | — | — | 0.06% |
| Total Impurities | | 0.04% | 0.15% | 0.25% | 0.54% |

3G. Stability of Form. #7A (with Sod. Ascorbate and Edetate Disodium Dihydrate) Stored at 55° C.

| | RRT | T = 0 | 2 Weeks | 4 Weeks | 8 Weeks |
|---|---|---|---|---|---|
| Assay (%) | | 100.00 | 100.91 | 100.92 | 102.05 |
| Impurity C | 0.66 | ND | 0.06% | 0.05% | 0.11% |
| Impurity A | 0.81 | BQL | 0.11% | 0.22% | 0.17% |
| Impurity F | 0.93 | ND | ND | ND | ND |
| Impurity D | 1.14 | ND | ND | ND | ND |
| Impurity E | 2.85 | 0.06% | 0.07% | 0.06% | 0.11% |
| Impurity B | 3.21 | ND | ND | ND | 0.13% |
| Unknown | 0.50 | — | — | — | 0.05% |
| Impurities | 2.41 | — | — | — | 0.05% |
| Total Impurities | | 0.06% | 0.24% | 0.33% | 0.62% |

Similar to the stability study at 40° C., all of the formulations of the present invention had significantly fewer impurities at eight weeks compared to the control. The superior stability characteristics of the formulations of the present invention will allow the formulations to be effective when used by patients.

Example 3: Droplet Testing

In order to determine the spray profile of Formulation #5A, it was subjected to standardized droplet testing. A challenge of creating a Naloxone sublingual and/or intranasal spray formulation is that it must be capable of producing spray droplets that are over 10 microns in diameter. Spray droplets 10 microns or smaller could be inhaled into the lungs. The optimal particle size for sublingual and intranasal spray droplets is from 20 to about 200 microns in diameter. It is desirable for the formulation to have droplet sizes near 20 because this increases the surface area and increased surface area exposure is one factor that contributes to a high bioavailability. Sublingual and intranasal formulations should be able to maintain a consistent droplet size throughout its shelf life.

Droplet analysis was conducted using standard laser analysis procedures known by those of skill in the art. Droplet size distribution (Dv10, Dv50, Dv90, and Span were tested at two distances, 3 cm and 6 cm). Dv10 refers to droplet size for which 10% of the total volume is obtained; Dv50 refers to droplet size for which 50% of the total volume is obtained; Dv90 refers to droplet size for which 90% of the total volume is obtained; Span refers to distribution span (Dv90–Dv10)/Dv50; % RSD refers to the percent relative standard deviation. The results of these tests can be seen below in Tables 4 to 9. Applicant found during testing that formulations of the present invention yielded desirable droplet sizes for sublingual and intranasal administration. The testing also revealed that the formulation dose remains consistent when administered with a spray pump.

TABLE 4

Spray Profile of Naloxone Spray Formulation #5A, Particle Size at 3 cm

| | Particle Size | | | | |
|---|---|---|---|---|---|
| Formulation #5A | DV(10) | DV(50) | DV(90) | % < 10µ | Span |
| 3 cm Actuation 1 | 14.79 | 28.92 | 389.9 | 1.225 | 12.97 |
| Actuation 2 | 17.98 | 32.05 | 455.6 | 0.001 | 13.65 |
| Actuation 3 | 13.46 | 36.92 | 584.8 | 4.747 | 15.48 |
| Average | 15.41 | 32.63 | 476.8 | 1.991 | 14.03 |

TABLE 5

Spray Profile of Naloxone Spray Formulation #5A, Particle Size at 6 cm

| | Particle Size | | | | |
|---|---|---|---|---|---|
| Formulation #5A | DV(10) | DV(50) | DV(90) | % < 10µ | Span |
| 6 cm Actuation 1 | 20.58 | 38.64 | 498.6 | 1.918 | 12.37 |
| Actuation 2 | 18.67 | 37.59 | 529.4 | 1.537 | 13.59 |
| Actuation 3 | 21.26 | 36.44 | 452.3 | 1.767 | 11.83 |
| Average | 20.17 | 37.56 | 493.4 | 1.741 | 12.60 |

TABLE 6

Spray Profile of Naloxone Spray Formulation #5A, Spray Pattern at 3 cm

| Formulation #5A | | Spray Pattern | | |
| --- | --- | --- | --- | --- |
| | | Dmin (mm) | Dmax (mm) | Ovality Ratio |
| 3 cm | Actuation 1 | 21.2 | 33.4 | 1.577 |
| | Actuation 2 | 23.5 | 31.5 | 1.342 |
| | Actuation 3 | 17.6 | 30.9 | 1.755 |
| | Average | 20.8 | 31.9 | 1.558 |

TABLE 7

Spray Profile of Naloxone Spray Formulation #5A, Spray Pattern at 6 cm

| Formulation #5A | | Spray Pattern | | |
| --- | --- | --- | --- | --- |
| | | Dmin (mm) | Dmax (mm) | Ovality Ratio |
| 6 cm | Actuation 1 | 24.5 | 55.6 | 2.268 |
| | Actuation 2 | 34.3 | 49.7 | 1.447 |
| | Actuation 3 | 33.9 | 52 | 1.535 |
| | Average | 30.9 | 52.4 | 1.750 |

TABLE 8

Spray Profile of Naloxone Spray Formulation #5A, Plume geometry data at 3 cm

| Formulation #5A | | Plume Geometry | |
| --- | --- | --- | --- |
| | | Width (mm) | Angle (°) |
| 3 cm | Actuation 1 | 28.7 | 51.1 |
| | Actuation 2 | 25.5 | 45.9 |
| | Actuation 3 | 35.4 | 60.4 |
| | Average | 29.9 | 52.5 |

TABLE 9

Spray Profile of Naloxone Spray Formulation #5A, Plume geometry data at 6 cm

| Formulation #5A | | Plume Geometry | |
| --- | --- | --- | --- |
| | | Width (mm) | Angle (°) |
| 6 cm | Actuation 1 | 54.3 | 48.4 |
| | Actuation 2 | 52.6 | 47.3 |
| | Actuation 3 | — | — |
| | Average | 53.5 | 47.9 |

As can be seen in Tables 4 to 9, Formulation #5A of the present invention provided excellent plume geometry and spray patterns.

Example 4: Preparation of Naloxone Formulations that are Alcohol-Free

In order to prepare a naloxone liquid formulation, the components as indicated in "Table 10. The Components of Formulation #1AF" below were weighed. The components were mixed until a clear solution was formed.

Naloxone HCL dihydrate base U.S.P. was used as the source of naloxone in the formulations that follow. Methyl paraben, U.S.P., (available from Spectrum) was used as the preservative source. Strawberry flavor, Nat&Art 915.0543 U, (available from FONA) was used as the source of flavoring agent. Edetate Disodium Dihydrate, U.S.P., (available from Spectrum) was used as the source of chelating agent or as antioxidant. Water, U.S.P., purified, (available from RICCA) was used as the source of solvent.

TABLE 10

The Components of Formulation #1AF

| Ingredients | % w/w |
| --- | --- |
| Naloxone HCl Dihydrate | 4.82 |
| Sucralose | 0.80 |
| Methyl Paraben | 0.10 |
| Flavoring agent | 0.08 |
| Edetate Disodium Dihydrate | 0.05 |
| Water USP | 94.15 |
| | 100.0 |

Example 5. Preparation of Additional Naloxone Liquid Formulations

In order to prepare naloxone liquid formulations, the components as indicated in "Table 11. The Components of Control and Formulations #1AF to #6AF" below were weighed. The components were mixed until a clear solution was formed.

Strawberry flavoring was used as the source of flavoring agent.

TABLE 11

The Components of Control and Formulations #1AF to #6AF

| Formulation | Control | #1AF | #2AF | #3AF | #4AF | #5AF | #6AF |
| --- | --- | --- | --- | --- | --- | --- | --- |
| Naloxone HCL Dihydrate | 4.83 | 4.82 | 4.89 | 4.89 | 4.89 | 4.83 | 4.82 |
| Water (USP) | 94.19 | 94.15 | 95.01 | 94.08 | 93.98 | 94.16 | 94.15 |
| Sucralose | 0.8 | 0.8 | | 0.8 | 0.8 | 0.8 | 0.8 |
| Methyl Paraben | 0.1 | 0.1 | | 0.1 | 0.1 | 0.1 | 0.1 |
| Flavoring | 0.08 | 0.08 | 0.08 | 0.08 | 0.08 | 0.08 | 0.08 |
| Edetate Disodium Dihydrate | | 0.05 | 0.005 | 0.05 | 0.05 | 0.005 | 0.05 |
| L-cysteine Hydrochloride Monohydrate | | | | | 0.1 | | |
| Sodium Ascorbate | | | 0.02 | | | 0.02 | |
| pH | 3.03 | 2.5 | 4.46 | 4.16 | 2.56 | 3.02 | 3 |

Example 6: Stability Testing of Naloxone Formulations

The formulations listed in Table 11 were subjected to stability testing at 40° C. and 55° C.±2° C. under 75%±5% relative humidity for eight weeks. The stability data was collected at zero, one, two, three, four, at 55° C. and at zero, four weeks at 40° C. Assay and impurities were detected using high performance liquid chromatography with an ultraviolet detector. The assay was performed at 288 nm and indicated as a % of initial concentration. For all impurities, analysis was performed at 240 nm and expressed as a % area. Amounts of particular impurities are listed in Tables 12A to 12G and 13A to 13C as a percentage of the area of each formulation along with amount of total impurities. "BQL" refers to "Below Quantifiable Limit" and "ND" refers to "Not Detected." "Ppm" refers to parts per million.

Tables 12A to 12G. Stability Data for Liquid Naloxone Spray Formulations Stored at 55° C.

12A. Stability of Control Stored at 55° C.

| Naloxone | RRT | T = 0 | 1 Week 55° C. |
|---|---|---|---|
| Assay (%) |  | 100 | 101.48 |
| Impurity C | 0.66 | ND | ND |
| Impurity A | 0.83 | 0.15 | 0.15 |
| Impurity F | 0.93 | ND | ND |
| Impurity D | 1.14 | ND | ND |
| Impurity E | 3.20 | 0.07 | 0.62 |
| Impurity B | 3.40 | ND | ND |
| Unknown | 0.49 | — | 0.07 |
| Impurities | 0.59 | — | 0.12 |
| Total Impurities |  | 0.22% | 0.96% |

12B. Stability of Form. #2AF (with Sod. ascorbate & Edetate Disodium Dihydrate) Stored at 55° C.

| Naloxone | RRT | T = 0 | 1 Week | 2 Weeks | 3 Weeks | 4 Weeks |
|---|---|---|---|---|---|---|
| pH |  | 4.469 | 4.21 | 4.239 | 4.02 | 4.224 |
| Assay (%) |  | 100 | 99.6 | 101.48 | 98.07 | 98.00 |
| Impurity C | 0.66 | ND | BQL | BQL | BQL | BQL |
| Impurity A | 0.83 | BQL | 0.09 | 0.28 | 0.27 | 0.18% |
| Impurity F | 0.93 | ND | ND | ND | ND | ND |
| Impurity D | 1.14 | ND | ND | ND | ND | ND |
| Impurity E | 3.20 | ND | ND | ND | ND | ND |
| Impurity B | 3.40 | ND | ND | ND | ND | ND |
| Unknown Impurities | 0.33 | — | — | 0.07 | 0.1 | 0.13 |
|  | 0.49 | — | — | 0.05 | 0.07 | 0.07% |
|  | 0.56 | — | 0.08 | 0.08 | 0.09 | 0.08 |
|  | 0.59 | — | 0.07 | 0.12 | 0.14 | 0.14 |
|  | 3.90 | — | 0.09 | 0.15 | 0.13 | 0.14 |
| Total Impurities |  | 0.00% | 0.33% | 0.82% | 0.80% | 0.74% |

12C. Stability of Form. #3AF (Edetate Disodium Dihydrate) Stored at 55° C.

| Naloxone | RRT | T = 0 | 1 Weeks | 2 Weeks | 3 Weeks | 4 Weeks |
|---|---|---|---|---|---|---|
| pH |  | 4.16 | 4.23 | 4.168 | 3.94 | 4.33 |
| Assay (%) |  | 100 | 100.5 | 100.7 | 98.03 | 98.63 |
| Impurity C | 0.66 | ND | ND | ND | ND | ND |
| Impurity A | 0.83 | BQL | BQL | 0.21 | 0.18 | 0.07 |
| Impurity F | 0.93 | ND | ND | ND | ND | ND |
| Impurity D | 1.14 | ND | ND | ND | ND | ND |
| Impurity E | 3.20 | 0.13 | 0.11 | 0.09 | 0.09 | 0.08 |
| Impurity B | 3.40 | ND | ND | ND | ND | ND |
| Unknown Impurities | 0.33 | — | — | 0.11 | 0.12 | 0.18 |
|  | 0.49 | — | — | 0.09 | 0.1 | 0.11% |
|  | 0.59 | ND | 0.12 | 0.11 | 0.14 | 0.15 |
|  | 3.67 | — | — | — | — | 0.07 |
|  | 3.90 | — | 0.08 | 0.14 | 0.13 | 0.13 |
| Total Impurities |  | 0.13% | 0.31% | 0.72% | 0.76% | 0.79% |

12D. Stability of Form. #4AF
(Edetate Disodium Dihydrate and L-Cysteine hydrochloride) Stored at 55° C.

| Naloxone | RRT | T = 0 | 1 Week | 2 Weeks | 3 Weeks | 4 Weeks |
|---|---|---|---|---|---|---|
| pH | | 2.56 | 2.5 | 2.44 | 2.38 | 2.413 |
| Assay (%) | | 100 | 98.5 | 100.03 | 97.87 | 98.59 |
| Impurity C | 0.66 | ND | ND | 0.13 | 0.11 | 0.09% |
| Impurity A | 0.83 | BQL | ND | 0.22 | 0.29 | 0.17% |
| Impurity F | 0.93 | ND | ND | ND | ND | ND |
| Impurity D | 1.14 | ND | ND | ND | ND | ND |
| Impurity E | 3.20 | ND | ND | ND | ND | ND |
| Impurity B | 3.40 | ND | ND | ND | ND | ND |
| Unknown Impurities | 0.56 | ND | ND | 0.05 | 0.07 | 0.06 |
| Total Impurities | | 0.00% | 0.00% | 0.40% | 0.47% | 0.32% |

12E. Stability of Form. #5AF (Edetate Disodium dihydrate and Sodium ascorbate) Stored at 55° C.

| Naloxone | RRT | T = 0 | 1 Week | 2 Weeks |
|---|---|---|---|---|
| pH | | NP | NP | 3.185 |
| Assay (%) | | 100 | 98.37 | 98.12 |
| Impurity C | 0.66 | ND | BQL | BQL |
| Impurity A | 0.83 | 0.15 | 0.18 | 0.11 |
| Impurity F | 0.93 | ND | ND | ND |
| Impurity D | 1.14 | ND | ND | ND |
| Impurity E | 3.20 | 0.07 | 0.16 | 0.12 |
| Impurity B | 3.40 | ND | ND | ND |
| Total Impurities | | 0.22% | 0.34% | 0.23% |

12F. Stability of Form. #6AF (Edetate Disodium Dihydrate) Stored at 55° C.

| Naloxone | RRT | T = 0 | 1 Week | 2 Weeks | 3 Weeks | 4 Weeks |
|---|---|---|---|---|---|---|
| pH | | 3.013 | 3.443 | 3.132 | 3.241 | 3.21 |
| Assay (%) | | 100.00% | 98.34% | 98.36% | 98.34% | 100.07% |
| Impurity C | 0.66 | 0.10% | 0.10% | 0.21% | 0.13% | 0.13% |
| Impurity A | 0.83 | BQL | BQL | BQL | BQL | BQL |
| Impurity F | 0.93 | ND | ND | ND | ND | ND |
| Impurity D | 1.14 | ND | 0.83 ppm | 1.79 ppm | 1.74 ppm | ND |
| Impurity E | 3.20 | 0.15% | 0.15% | 0.15% | 0.17% | 0.17% |
| Impurity B | 3.40 | ND | ND | ND | ND | ND |
| Unknown Impurities | 0.49 | — | — | 0.06% | 0.06% | 0.12% |
| | 0.77 | — | — | BQL | BQL | 0.05% |
| Total Impurities | | 0.25% | 0.25% | 0.42% | 0.36% | 0.47% |

12G. Stability of Form. #1AF (Edetate Disodium Dihydrate) Stored at 55° C.

| Naloxone | RRT | T = 0 | 1 Week | 2 Weeks | 3 Weeks | 4 Weeks |
|---|---|---|---|---|---|---|
| pH | | 2.505 | 2.907 | 2.581 | 2.616 | 2.62 |
| Assay (%) | | 100.00% | 107.80% | 100.51% | 100.17% | 102.39% |
| Impurity C | 0.66 | 0.10% | 0.10% | 0.10% | 0.10% | 0.09% |
| Impurity A | 0.83 | BQL | BQL | BQL | BQL | BQL |
| Impurity F | 0.93 | ND | ND | ND | ND | ND |
| Impurity D | 1.14 | NP | 0.95 ppm | 1.25 ppm | 1.59 ppm | ND |
| Impurity E | 3.20 | 0.15% | 0.14% | 0.15% | 0.16% | 0.18% |
| Impurity B | 3.40 | ND | ND | ND | ND | ND |
| Unknown Impurities | 0.06 | 0.13% | 0.13% | 0.13% | 0.13% | ND |
| | 0.49 | — | — | 0.08% | 0.06% | 0.05% |
| | 4.63 | ND | ND | ND | BQL | ND |
| Total Impurities | | 0.38% | 0.37% | 0.46% | 0.45% | 0.32% |

Liquid naloxone formulations of the present invention contained less than 0.8% of total impurities after four weeks at 55° C. This is a stark contrast to the control formulation which contained 0.96% impurities after 1 week at 55° C. Specifically, the formulations which contained sodium ascorbate or edetate disodium dihydrate exhibited lower impurities after four weeks. Additionally, the formulations which contained edetate disodium dihydrate were very stable.

Tables 13A to 13C. Stability Data for Liquid Naloxone Spray Formulations Stored at 40° C. Under 75% Relative Humidity 13A. Stability of Form. #2AF (with Sod. ascorbate & Edetate Disodium Dihydrate) Stored at 40° C. under 75% Relative Humidity

| Naloxone | RRT | T = 0 | 4 Weeks |
|---|---|---|---|
| pH | | 4.469 | 4.394 |
| Assay (%) | | 100 | 98.12 |
| Impurity C | 0.66 | ND | 0.06 |
| Impurity A | 0.83 | BQL | 0.12 |
| Impurity F | 0.93 | ND | ND |
| Impurity D | 1.14 | ND | ND |
| Impurity E | 3.20 | ND | ND |
| Impurity B | 3.40 | ND | ND |
| Unknown Impurities | 0.49 | ND | 0.06 |
| | 0.59 | ND | 0.06 |
| | 3.90 | ND | 0.14 |
| Total Impurities | | 0.00% | 0.44% |

13B. Stability of Form. #3AF (Edetate Disodium Dihydrate) Stored at 40° C. under 75% Relative Humidity

| Naloxone | RRT | T = 0 | 4 Weeks |
|---|---|---|---|
| pH | | 4.16 | 4.596 |
| Assay (%) | | 100 | 99.69 |
| Impurity C | 0.66 | ND | ND |
| Impurity A | 0.83 | BQL | BQL |
| Impurity F | 0.93 | ND | ND |
| Impurity D | 1.14 | ND | ND |
| Impurity E | 3.20 | 0.13 | ND |
| Impurity B | 3.40 | ND | ND |
| Unknown Impurities | 0.59 | ND | 0.11 |
| | 3.90 | ND | 0.11 |
| Total Impurities | | 0.13% | 0.22% |

13C. Stability of Form. #4AF (Edetate Disodium Dihydrate and L-Cysteine hydrochloride) Stored at 40° C. under 75% Relative Humidity

| Naloxone | RRT | T = 0 | 4 Weeks |
|---|---|---|---|
| pH | | 2.56 | 2.502 |
| Assay (%) | | 100 | 97.08 |
| Impurity C | 0.66 | ND | ND |
| Impurity A | 0.83 | BQL | BQL |
| Impurity F | 0.93 | ND | ND |
| Impurity D | 1.14 | ND | ND |
| Impurity E | 3.20 | ND | ND |
| Impurity B | 3.40 | ND | ND |
| Total Impurities | | 0.00% | 0.00% |

The naloxone formulations of the present invention contained less than 0.45% of total impurities after four weeks at 40° C.

Example 7: Freeze/Thaw Testing

In order to further determine the stability of Formulations #1AF and #6AF, the formulations were subjected to standard freeze/thaw stability testing. The results are below in "Table 14. Stability of Formulations #1AF and #6AF to Freeze/Thaw Testing."

TABLE 14

Stability of Formulations #1AF and #6AF to Freeze/Thaw Testing

| Formulation #1AF to #6AF | Drug Substance | t = 0 | Cycle 1, −20° C. (2 Days) | Cycle 1, 25° C. (2 Days) | Cycle 2, −20° C. (2 Days) | Cycle 2, 25° C. (2 Days) | Cycle 3, −20° C. (2 Days) | Cycle 3, 25° C. (2 days) |
|---|---|---|---|---|---|---|---|---|
| Physical appearance | clear | clear | clear | clear | clear | clear | clear | clear |
| Color | colorless | colorless | colorless | colorless | colorless | colorless | colorless | Colorless |

The naloxone formulations #1AF to #6AF were clear and colorless after several cycles of freezing and thawing. This study further demonstrates the stability of the formulations.

Example 8: Droplet Testing

In order to determine the spray profile of Formulation #1AF, it was subjected to standardized droplet testing. As previously explained, the optimal particle size for sublingual and intranasal spray droplets is from 20 to about 200 microns in diameter. It is desirable for the formulation to have droplet sizes near 20 because this increases the surface area and increased surface area exposure is one factor that contributes to a high bioavailability. Sublingual and intranasal formulations should be able to maintain a consistent droplet size throughout its shelf life.

Droplet analysis was conducted using standard laser analysis procedures known by those of skill in the art.

Droplet size distribution (Dv10, Dv50, Dv90, and Span were tested at two distances, 3 cm and 6 cm). Dv10 refers to droplet size for which 10% of the total volume is obtained; Dv50 refers to droplet size for which 50% of the total volume is obtained; Dv90 refers to droplet size for which 90% of the total volume is obtained; Span refers to distribution span (Dv90−Dv10)/Dv50; % RSD refers to the percent relative standard deviation. The results of these tests can be seen below in Tables 15 to 20. Applicant found during testing that formulations of the present invention yielded desirable droplet sizes for sublingual and intranasal administration. The testing also revealed that the formulation dose remains consistent when administered with a spray pump.

TABLE 15

Spray Profile of Naloxone Spray Formulation #1AF, Particle Size at 3 cm

| Formulation #1AF | | DV(10) | DV(50) | DV(90) | %<10 μ | Span |
|---|---|---|---|---|---|---|
| 3 cm | Actuation 1 | 13.16 | 26.23 | 63.21 | 2.792 | 1.908 |
| | Actuation 2 | 11.52 | 27 | 90.85 | 6.547 | 2.939 |
| | Actuation 3 | 12.95 | 28.39 | 144 | 3.505 | 4.615 |
| | Average | 12.54 | 27.21 | 99.4 | 4.281 | 3.15 |

TABLE 16

Spray Profile of Naloxone Spray Formulation #1AF, Particle Size at 6 cm

| Formulation #1AF | | DV(10) | DV(50) | DV(90) | %<10 μ | Span |
|---|---|---|---|---|---|---|
| 6 cm | Actuation 1 | 20.18 | 32.51 | 53.9 | 1.198 | 1.037 |
| | Actuation 2 | 18.02 | 31.45 | 58.48 | 0.024 | 1.286 |
| | Actuation 3 | 16.81 | 33.44 | 77.92 | 1.799 | 1.828 |
| | Average | 18.34 | 32.47 | 63.4 | 1.007 | 1.38 |

TABLE 17

Spray Profile of Naloxone Spray Formulation #1AF, Spray Pattern at 3 cm

| | | Spray Pattern | | |
|---|---|---|---|---|
| Formulation #1AF | | Dmin (mm) | Dmax (mm) | Ovality Ratio |
| 3 cm | Actuation 1 | 26.5 | 41.3 | 1.557 |
| | Actuation 2 | 24.8 | 43.5 | 1.751 |
| | Actuation 3 | 29 | 40.6 | 1.402 |
| | Average | 26.8 | 41.8 | 1.570 |

TABLE 18

Spray Profile of Naloxone Spray Formulation #1AF, Spray Pattern at 6 cm

| | | Spray Pattern | | |
|---|---|---|---|---|
| Formulation #1AF | | Dmin (mm) | Dmax (mm) | Ovality Ratio |
| 6 cm | Actuation 1 | 52.6 | 68.6 | 1.304 |
| | Actuation 2 | 40.3 | 61.4 | 1.524 |
| | Actuation 3 | 47.5 | 59.7 | 1.256 |
| | Average | 46.8 | 63.2 | 1.361 |

TABLE 19

Spray Profile of Naloxone Spray Formulation #1AF, Plume geometry data at 3 cm

| | | Plume Geometry | |
|---|---|---|---|
| Formulation #1AF | | Width (mm) | Angle (°) |
| 3 cm | Actuation 1 | 39.7 | 66.7 |
| | Actuation 2 | 37.7 | 64.3 |
| | Actuation 3 | 33.5 | 58 |
| | Average | 37.0 | 63.0 |

TABLE 20

Spray Profile of Naloxone Spray Formulation #1AF, Plume geometry data at 6 cm

| | | Plume Geometry | |
|---|---|---|---|
| Formulation #1AF | | Width (mm) | Angle (°) |
| 6 cm | Actuation 1 | 63 | 54.9 |
| | Actuation 2 | 67.1 | 58.3 |
| | Actuation 3 | 68 | 59 |
| | Average | 66.0 | 57.4 |

As can be seen in Tables 15 to 20, Formulation #1AF of the present invention provided excellent plume geometry and spray patterns.

Example 9. Preparation of Additional Naloxone Liquid Formulations

In order to prepare naloxone liquid formulations, the components as indicated in "Table 21. The Components of Formulations #8A, #9A, #7AF and #8AF" below were weighed. The components were mixed until a clear solution was formed.

Strawberry flavoring was used as the source of flavoring agent.

TABLE 21

The Components of Formulations #8A, #9A, #7AF and #8AF

| Formulation | Control | #8A | #9A | #7AF | #8AF |
|---|---|---|---|---|---|
| Naloxone | 2.44 | 10.419 | 10.265 | 4.4196 | 4.4196 |
| Water (USP) | 37.56 | 29.506 | 31.324 | 94.769 | 94.779 |
| Ethanol | 55 | 55 | 50 | | |
| Propylene Glycol | 5 | 5 | 5 | | |
| L-menthol | | 0.05 | 0.5 | | |
| BKC | | | 0.01 | 0.01 | |
| Sodium Chloride | | | | 0.8 | 0.8 |
| Flavoring agent | | | 0.08 | | |
| Edetate disodium dihydrate | 0.005 | 0.001 | 0.001 | 0.001 | |
| Sucralose | | | 0.8 | | |
| Caprylic Acid | | | 2 | | |
| Sodium Ascorbate | | 0.02 | 0.02 | | | pH-4.5 ± 0.2

Example 10. Preparation of Additional Naloxone Nasal Spray Formulations

In order to prepare naloxone liquid formulations, the components as indicated in Tables 22, 23 and 24 below were weighed. The components were mixed until a clear solution was formed.

TABLE 22

Stable Naloxone Nasal Spray Formulations

|  | #10A | #11A | #12A | #13A | #14A | #15A | #16A |
| --- | --- | --- | --- | --- | --- | --- | --- |
| Naloxone | 9.49 | 8.85 | 8.75 | 8.57 | 4.0 | 8.75 | 8.75 |
| Water (USP) | 35.505 | 66.14 | 71.135 | 79.31 | 83.88 | 81.135 | 81.135 |
| Ethanol | 50.0 | 20.0 | 10.0 | 2.0 | 2.0 | 10.0 | 10.0 |
| Propylene Glycol | 5.0 | 5.0 | 10.0 | 10.0 | 10.0 | — | — |
| Edetate disodium dihydrate (EDTA) | 0.005 | 0.01 | 0.015 | 0.02 | 0.02 | 0.015 | 0.015 |
| Methyl Paraben | — | — | 0.1 | 0.1 | 0.1 | 0.1 | 0.1 |
| pH | 4.5 ± 0.1 | 4.5 ± 0.1 | 4.5 ± 0.1 | 4.5 ± 0.1 | 4.5 ± 0.1 | 4.5 ± 0.1 | 3.0 ± 0.1 |

TABLE 23

Stable Naloxone Nasal Spray Formulations

|  | #17A | #18A | #19A | #20A |
| --- | --- | --- | --- | --- |
| Naloxone | 2.405 | 2.52 | 4.788 | 4.477 |
| Water (USP) | 42.594 | 72.738 | 40.207 | 40.513 |
| Ethanol | 50.0 | 20.0 | 50.0 | 20.0 |
| Propylene Glycol | 5.0 | 5.0 | 5.0 | 5.0 |
| Edetate disodium dihydrate (EDTA) | 0.005 | 0.01 | 0.005 | 0.01 |
| pH | 4.5 ± 0.1 | 4.5 ± 0.1 | 4.5 ± 0.1 | 4.5 ± 0.1 | values = % w/w

TABLE 24

Stable Non-Alcoholic Naloxone Nasal Spray Formulations

|  | #9AF | #10AF | #11AF | #12AF |
| --- | --- | --- | --- | --- |
| Naloxone | 4.83 | 4.4 | 8.55 | 4.0 |
| Water (USP) | 95.02 | 90.495 | 81.33 | 85.88 |
| Propylene Glycol | — | 5.0 | 10.0 | 10.0 |
| EDTA | 0.05 | 0.005 | 0.02 | 0.02 |
| Methyl Paraben | 0.1 | 0.1 | 0.1 | 0.1 |
| pH | 3.0 ± 0.1 | 4.5 ± 0.1 | 4.5 ± 0.1 | 4.5 ± 0.1 | values = % w/w

All formulations of Tables 22, 23 and 24 were stable upon mixing. Formulations of Tables 22, 23 and 24 differ from prior art naloxone nasal spray formulations because the formulations of Tables 22, 23 and 24 do not contain an isotonicity agent, specifically sodium chloride, a buffer, specifically citric acid, an anti-microbial agent, specifically benzyl alcohol or benzalkonium chloride. Further, formulations of Tables 22, 23 and 24 contain EDTA at a concentration of no more than 0.05% w/w.

TABLE 25

Stability of Formulations # 9A and # 8A to Freeze/Thaw Testing

| Formulation | Drug Substance | t = 0 | Cycle 1, −20° C. (2days) | Cycle 1, 40° C. (2 days) | Cycle 2, −20° C. (2 days) | Cycle 2, 40° C. (2 days) | Cycle 3, −20° C. (2 Days) | Cycle 3, 40° C. (2 Days) |
| --- | --- | --- | --- | --- | --- | --- | --- | --- |
| Physical appearance | clear | clear | clear | clear | clear | Clear | clear | clear |
| Color | colorless | colorless | colorless | colorless | colorless | colorless | colorless | Colorless |

The naloxone formulations #8A and #9A were clear and colorless after several cycles of freezing and thawing. This study further demonstrates the stability of the formulations.

Formulations #10A and #11A were also subjected to freeze/thaw testing to evaluate physical stability. Each 2 ml of formulation was filled in a glass vial and placed in freeze-thaw chamber and subjected to temperature cycling's. Study consist of 12-hour cycles, with temperatures ranging between freezer temperature (−10 to −20° C.) and 40° C. for a period of at least 4 weeks. Results shows that all formulations are clear and colorless during the study.

Example 11: Droplet Testing

In order to determine the spray profile of Formulation #9A, it was subjected to standardized droplet testing. As previously explained, the optimal particle size for sublingual and intranasal spray droplets is from 20 to about 200 microns in diameter. It is desirable for the formulation to have droplet sizes near 20 because this increases the surface area and increased surface area exposure is one factor that contributes to a high bioavailability. Sublingual and intranasal formulations should be able to maintain a consistent droplet size throughout its shelf life.

Droplet analysis was conducted using standard laser analysis procedures known by those of skill in the art. Droplet size distribution (Dv10, Dv50, Dv90, and Span were tested at two distances, 3 cm and 6 cm). Dv10 refers to droplet size for which 10% of the total volume is obtained; Dv50 refers to droplet size for which 50% of the total volume is obtained; Dv90 refers to droplet size for which 90% of the total volume is obtained; Span refers to distribution span (Dv90−Dv10)/Dv50; % RSD refers to the percent relative standard deviation. The results of these tests can be seen below in Tables 26 to 41. Applicant found during testing that formulations of the present invention yielded desirable droplet sizes for sublingual and intranasal administration. The testing also revealed that the formulation dose remains consistent when administered with a spray pump.

TABLE 26

Spray Profile of naloxone Spray Formulation #9A, Particle Size at 3 cm

| Formulation #9A | DV(10) | DV(50) | DV(90) | %<10 μ | Span |
|---|---|---|---|---|---|
| 3 cm Actuation 1 | 23.06 | 44.28 | 99.7 | 0 | 1.731 |
| Actuation 2 | 22.08 | 44.34 | 104.4 | 0.661 | 1.856 |
| Actuation 3 | 22.27 | 55.05 | 107.5 | 1.012 | 2.82 |
| Average | 22.47 | 47.89 | 103.9 | 0.558 | 2.14 |

TABLE 27

Spray Profile of Naloxone Spray Formulation #9A, Particle Size at 6 cm

| Formulation #9A | DV(10) | DV(50) | DV(90) | % < 10μ | Span |
|---|---|---|---|---|---|
| 6 cm Actuation 1 | 28.54 | 51.29 | 91.87 | 2.113 | 1.235 |
| Actuation 2 | 25.75 | 50.01 | 103.7 | 1.594 | 1.56 |
| Actuation 3 | 31.99 | 51.77 | 85 | 0 | 1.024 |
| Average | 28.76 | 51.02 | 93.5 | 1.236 | 1.27 |

TABLE 28

Spray Profile of Naloxone Spray Formulation #9A, Spray Pattern at 3 cm

| Formulation #9A | | Dmin (mm) | Dmax (mm) | Ovality Ratio |
|---|---|---|---|---|
| 3 cm | Actuation 1 | 14.7 | 22.7 | 1.544 |
| | Actuation 2 | 14.4 | 21.8 | 1.517 |
| | Actuation 3 | 15.2 | 20.9 | 1.372 |
| | Average | 14.8 | 21.8 | 1.478 |

TABLE 29

Spray Profile of Naloxone Spray Formulation #9A, Spray Pattern at 6 cm

| Formulation #9A | | Dmin (mm) | Dmax (mm) | Ovality Ratio |
|---|---|---|---|---|
| 6 cm | Actuation 1 | 23.5 | 30.4 | 1.291 |
| | Actuation 2 | 24.5 | 41.8 | 1.707 |
| | Actuation 3 | 20.5 | 32.7 | 1.597 |
| | Average | 22.8 | 35.0 | 1.532 |

TABLE 30

Spray Profile of Naloxone Spray Formulation #9A, Plume geometry data at 3 cm

| Formulation #9A | | Width (mm) | Angle (°) |
|---|---|---|---|
| 3 cm | Actuation 1 | 22.5 | 39.9 |
| | Actuation 2 | 15.5 | 28.6 |
| | Actuation 3 | 25.7 | 44.3 |
| | Average | 21.2 | 37.6 |

TABLE 31

Spray Profile of Naloxone Spray Formulation #9A, Plume geometry data at 6 cm

| Formulation #9A | | Width (mm) | Angle (°) |
|---|---|---|---|
| 6 cm | Actuation 1 | 26.4 | 24.3 |
| | Actuation 2 | 25 | 23.3 |
| | Actuation 3 | 37.6 | 33.2 |
| | Average | 29.7 | 26.9 |

TABLE 32

Spray Profile of Naloxone Spray Formulation # 10A, Particle Size at 3 cm

| Formulation # 10A | DV(10) | DV(50) | DV(90) | %<10 μ | Span |
|---|---|---|---|---|---|
| 3 cm Actuation 1 | 19.84 | 46.86 | 112.10 | 3.744 | 2.011 |
| Actuation 2 | 21.21 | 48.69 | 110.70 | 2.503 | 1.837 |
| Average | 20.53 | 47.77 | 111.40 | 1.924 | 3.124 |

TABLE 33

Spray Profile of Naloxone Spray Formulation # 10A, Spray Pattern at 3 cm

| Formulation # 10A | | Spray Pattern | | |
|---|---|---|---|---|
| | | Dmin (mm) | Dmax (mm) | Ovality Ratio |
| 3 cm | | 14.6 | 18.4 | 14.6 | 1.261 |
| | | 14.1 | 17.9 | 14.1 | 1.265 |
| | | 15.1 | 17.9 | 15.1 | 1.182 |
| | | 14.6 | 18.1 | 14.6 | 1.2 |

TABLE 34

Spray Profile of Naloxone Spray Formulation # 10A, Spray Pattern at 6 cm

| Formulation # 10A | Spray Pattern | | |
|---|---|---|---|
| | Dmin (mm) | Dmax (mm) | Ovality Ratio |
| 6 cm Actuation 1 | 23.7 | 29.8 | 1.259 |
| Actuation 2 | 20.2 | 31.6 | 1.566 |
| Actuation 3 | 22.0 | 32.0 | 1.453 |
| Average | 22.0 | 31.20 | 1.40 |

TABLE 35

Spray Profile of Naloxone Spray Formulation # 10A, Plume geometry data at 3 cm

| Formulation # 10A | Plume Geometry | |
|---|---|---|
| | Width (mm) | Angle (°) |
| 3 cm Actuation 1 | 36.7 | 19.97 |
| Actuation 2 | 36.82 | 19.97 |
| Average | 36.76 | 19.97 |

TABLE 36

Spray Profile of Naloxone Spray Formulation # 10A, Plume geometry data at 6 cm

| Formulation #10A | Plume Geometry | |
|---|---|---|
| | Width (mm) | Angle (°) |
| 6 cm Actuation 1 | 27.23 | 29.29 |
| Actuation 2 | 21.96 | 23.3 |
| Average | 24.60 | 26.30 |

TABLE 37

Spray Profile of Naloxone Spray Formulation # 11A, Particle Size at 3 cm

| Formulation # 11A | Particle Size | | | | |
|---|---|---|---|---|---|
| | DV(10) | DV(50) | DV(90) | %<10 μ | Span |
| 3 cm Actuation 1 | 15.7 | 38.14 | 90.81 | 4.56 | 1.969 |
| Actuation 2 | 15.11 | 37.9 | 86.75 | 5.09 | 1.89 |
| Average | 15.405 | 38.02 | 88.78 | 4.83 | 1.93 |

TABLE 38

Spray Profile of Naloxone Spray Formulation # 11A, Spray Pattern at 3 cm

| Formulation # 11A | Spray Pattern | | |
|---|---|---|---|
| | Dmin (mm) | Dmax (mm) | Ovality Ratio |
| 3 cm Actuation 1 | 15.9 | 22.4 | 1.410 |
| Actuation 2 | 18.8 | 20.4 | 1.086 |
| Actuation 3 | 16.2 | 22.5 | 1.392 |
| Average | 16.9 | 21.8 | 1.30 |

TABLE 39

Spray Profile of Naloxone Spray Formulation # 11A, Spray Pattern at 6 cm

| Formulation # 11A | Spray Pattern | | |
|---|---|---|---|
| | Dmin (mm) | Dmax (mm) | Ovality Ratio |
| 6 cm Actuation 1 | 20.8 | 29.4 | 1.411 |
| Actuation 2 | 20.8 | 31.1 | 1.495 |
| Actuation 3 | 23.1 | 31.8 | 1.376 |
| Average | 21.6 | 30.8 | 1.40 |

TABLE 40

Spray Profile of Naloxone Spray Formulation #11A, Plume geometry data at 3 cm

| Formulation #11A | Plume Geometry | |
|---|---|---|
| | Width (mm) | Angle (°) |
| 3 cm Actuation 1 | 31.30 | 19.98 |
| Actuation 2 | 36.63 | 19.97 |
| Average | 33.97 | 19.98 |

TABLE 41

Spray Profile of Naloxone Spray Formulation # 11A, Plume geometry data at 6 cm

| Formulation #11A | Plume Geometry | |
|---|---|---|
| | Width (mm) | Angle (°) |
| 6 cm Actuation 1 | 21.1 | 16.98 |
| Actuation 2 | 21.22 | 22.64 |
| Average | 21.16 | 19.81 |

As can be seen in Tables 26 to 41, Formulation #9A, #10A, and 11A of the present invention provided excellent plume geometry and spray patterns.

Example 12. Pharmacokinetic Analysis

The naloxone formulations described in Example 9, Table 21 of the instant specification were used. For formulations #7AF and #8AF a 4-mg dose was administered. For formulations #8A and #9A a 16-mg dose was administered.

Pharmacokinetic and Bioavailability Analysis

Protocol was a single dose crossover study. Five healthy male Yucatan minipigs weighing approximately forty kilograms each were sublingually administered the formulations of Table 21. The minipigs were fasted overnight and through four hours' post administration. Administration was followed by a one week washout period. Blood samples were taken prior to administration and 1, 3, 5, 7, 10, 15, 30 min, 1, 2, 4, 8 and 24 hours' post dose. Blood samples were measured for naloxone concentrations via liquid chromatography-tandem mass spectrometry.

The following pharmacokinetic parameters were calculated: peak concentration in plasma ($C_{max}$) and area under the concentration-time curve from time-zero to the time of the last quantifiable concentration ($AUC_{0-t}$).

Results and Conclusions

Results of the pharmacokinetic and statistical analysis for the naloxone formulations in Table 21 of the present invention are shown in Table 42.

TABLE 42

Summary of pharmacokinetic parameters for naloxone after sublingual administration of single doses of 4 mg and 16 mg of naloxone formulations to Yucatan minipigs under fasted conditions.

| Parameter* | #7AF | #8AF | #8A | #9A | #9A (repeat) |
|---|---|---|---|---|---|
| $C_{max}$ (ng/mL) | 8.9 ± 2.2 | 6.8 ± 2.2 | 26.3 ± 1.8 | 86.4 ± 2.4 | 58.6 ± 2.8 |
| Conc. @ 1 min (ng/mL) | NA | 0.1 | NA | 24.2 | NA |
| Conc. @ 3 min (ng/mL) | 0.2 | 0.3 | 5 | 68.5 | 12.9 |
| Conc. @ 5 min (ng/mL) | 1.4 | 1.9 | 6.3 | 62.7 | 36.9 |
| Conc. @ 7 min (ng/mL) | 1.6 | 2.6 | 9.1 | 28.8 | 50.5 |
| $AUC_{(0-t)}$ (ng * min/mL) | 746.2 ± 2.2 | 432.3 ± 2.0 | 2382.5 ± 2.0 | 3108.5 ± 2.2 | 3564.8 ± 2.8 |
| AUC @ 15 min (ng * min/mL) | 41.6 | 38 | 188.2 | 615.8 | 515.6 |
| AUC @ 30 min (ng * min/mL) | 151.8 | 106.8 | 504.4 | 987.4 | 1063.3 |

*Geometric mean ± geometric standard deviation. Sample size is 5.

The peak mean naloxone concentration was significantly higher for formulation #9A and #8A over #8AF and #7AF. Additionally, the area under the concentration-time curve from time-zero to the time of the last quantifiable concentration was significantly higher for formulations #9A and #8A over #8AF and #7AF. To determine if this result was based on the four-fold increase in the dose of naloxone in formulation #9A and #8A over #8AF and #7AF the geometric mean was normalized to 4 mg dose. See FIG. 1. A similar pattern remains even after normalization. Further, the peak mean naloxone concentration was significantly higher for formulation #9A, over #8A, which cannot be explained by the dosage as formulations #9A and #8A were each administered at 16 mg doses.

Additionally, formulation #9A reached about 80% of its peak mean naloxone concentration within 3 minutes of administration. In comparison, formulation #8A had reached only 35% of its peak mean naloxone concentration within 7 minutes, #8AF 38% in 7 minutes and #7AF 19% in 7 minutes. In a similar comparison formulation #9A reached 19% of its $AUC_{(0-t)}$ within 15 minutes of administration, #8A reached 7.9% in 15 minutes, #8AF reached 8.8% in 15 minutes and #7AF reached 5.6% in 15 minutes.

Administration of naloxone in formulations with co-solvents resulted in superior bioavailability. Compare formulation #9A and #8A to #8AF and #7AF. Further, the addition of permeation enhancers such as caprylic acid and BKC resulted in further increase in bioavailability. Compare formulations #9A to #8A and #7AF to #8AF.

Example 13. Stability Testing of Additional Naloxone Formulations

Formulation #9A, #10A, and 11A from Table 21 above was subjected to stability testing at 25° C./60% RH±5%, 40° C./75%±5% relative humidity and 55° C.±2° C. The stability data was collected at predetermined time points. Assay and impurities were detected using high performance liquid chromatography with an ultraviolet detector. The assay was performed at 288 nm and indicated as a % of initial concentration. For all impurities, analysis was performed at 240 nm and expressed as a % area. Amounts of particular impurities are listed in Tables 43 A to I as a percentage of the area of each formulation along with amount of total impurities.

TABLE 43A

Stability Data for the Formulation #9A Stored at 25° C. ± 2° C./60% ± 5% RH

| Naloxone Physical appearance (Clarity, Color) | RRT | T = 0 Clear, Colorless | 4 Weeks Clear, Colorless | 3 Months Clear, Colorless | 6 months Clear, Pale yellow |
|---|---|---|---|---|---|
| Assay (%) |  | 100 | 98.7 | 99.01 | 98.89 |
| Impurity C | 0.53 | ND | 0.01 | ND | ND |
| Impurity A | 0.63 | 0.02 | 0.03 | 0.02 | 0.04 |
| Impurity F | 0.93 | ND | ND | ND | ND |
| Impurity D | 1.14 | ND | ND | ND | ND |
| Impurity E | 1.42 | 0.05 | 0.02 | 0.02 | 0.03 |
| Impurity B | 1.87 | ND | ND | ND | ND |
| Unknown | 0.90 | ND | ND | 0.07 | 0.04 |
| Impurities | 1.48 | ND | 0.01 | 0.05 | 0.1 |
| Total Impurities |  | 0.07% | 0.07% | 0.16% | 0.21% |

ND = Not Detected ppm = parts per million

TABLE 43B

Stability Data for the Formulation #9A Stored at 40° C. ± 2° C./75% ± 5% RH

| Naloxone Physical appearance (Clarity, Color) | RRT | T = 0 Clear, Colorless | 4 Weeks Clear, light yellow | 3 Months Clear, light brownish yellow | 6 months Clear, light brownish yellow |
|---|---|---|---|---|---|
| Assay (%) | | 100 | 99.09 | 98.63 | 98.08 |
| Impurity C | 0.53 | ND | 0.01 | 0.01 | 0.02 |
| Impurity A | 0.63 | 0.02 | 0.04 | 0.06 | 0.16 |
| Impurity F | 0.93 | ND | ND | ND | ND |
| Impurity D | 1.14 | ND | ND | ND | ND |
| Impurity E | 1.42 | 0.05 | 0.01 | 0.01 | 0.02 |
| Impurity B | 1.87 | ND | ND | ND | ND |
| Unknown Impurities | 0.56 | ND | 0.05 | 0.04 | 0.10 |
| | 0.71 | ND | 0.04 | 0.03 | 0.06 |
| | 0.79 | ND | ND | 0.01 | 0.05 |
| | 0.90 | ND | ND | 0.05 | ND |
| | 1.23 | ND | ND | ND | 0.05 |
| | 1.27 | ND | ND | 0.02 | 0.05 |
| | 1.48 | ND | 0.07 | 0.14 | 0.21 |
| | 1.56 | ND | ND | ND | 0.07 |
| | 1.84 | ND | ND | 0.05 | 0.02 |
| Total Impurities | | 0.07% | 0.22% | 0.42% | 0.81% |

ND = Not Detected
ppm = parts per million

TABLE 43C

Stability Data for the Formulation # 9A Stored at 55° C. ± 20 C.

| Naloxone Physical appearance (Clarity, Color) | RRT | T = 0 Clear, Colorless | 4 Weeks Clear, yellow | 6 Weeks Clear, yellow | 8 Weeks Clear, yellow |
|---|---|---|---|---|---|
| Assay (%) | | 100 | 97.28 | 97.28 | 94.28 |
| Impurity C | 0.53 | ND | 0.03 | 0.03 | 0.04 |
| Impurity A | 0.63 | 0.02 | 0.21 | 0.28 | 0.39 |
| Impurity F | 0.93 | ND | ND | ND | ND |
| Impurity D | 1.14 | ND | 9.36 ppm | ND | ND |
| Impurity E | 1.42 | 0.05 | 0.05 | 0.05 | 0.05 |
| Impurity B | 1.87 | ND | ND | ND | ND |
| Unknown Impurities | 0.56 | ND | 0.13 | 0.14 | 0.19 |
| | 0.71 | ND | 0.06 | 0.07 | 0.06 |
| | 0.79 | ND | 0.08 | 0.11 | 0.19 |
| | 1.13 | ND | 0.01 | 0.05 | 0.05 |
| | 1.23 | ND | 0.04 | 0.06 | 0.08 |
| | 1.30 | ND | ND | ND | 0.06 |
| | 1.38 | ND | 0.02 | 0.06 | 0.12 |
| | 1.48 | ND | 0.11 | 0.12 | 0.13 |
| | 1.54 | ND | 0.06 | 0.07 | 0.15 |
| | 1.66 | ND | 0.03 | 0.05 | ND |
| Total Impurities | | 0.07% | 0.83% | 1.09% | 1.51% |

TABLE 43D

Stability Data for the Formulation # 10A Stored at 25° C. ± 2° C./60% ± 5% RH

| Naloxone | RRT | T = 0 | 1 Month | 2Months | 6 Months | 9 Months | 12 Months |
|---|---|---|---|---|---|---|---|
| Physical appearance (Clarity, Color) | | Clear, Colorless | Clear, Colorless | Clear, Colorless | Clear, Colorless | Clear, Colorless | Clear, Colorless |
| Assay (%) | | 100 | 101.44 | 104.95 | 101.64 | NP | 102.65 |
| Naloxone-N-oxide | | ND | ND | NP | NP | NP | NP |
| Impurity C | 0.53 | ND | ND | ND | ND | ND | 0.03 |
| Impurity A | 0.61 | ND | ND | 0.01 | 0.02 | 0.02 | 0.01 |
| Impurity F | 0.93 | ND | ND | ND | ND | ND | ND |
| Impurity D | 1.14 | ND | ND | ND | NP | NP | NP |
| Impurity E | 1.42 | 0.03 | 0.09 | 0.03 | 0.08 | 0.03 | 0.04 |
| Impurity B | 1.87 | ND | ND | ND | ND | ND | ND |
| Unknown Impurities | 0.71 | BQL | 0.05 | 0.06 | 0.06 | 0.06 | BQL |
| | 1.07 | 0.07 | 0.1 | 0.1 | 0.06 | 0.06 | 0.07 |
| | 1.33 | ND | ND | BQL | ND | ND | 0.07 |
| | 1.48 | ND | ND | ND | ND | ND | 0.06 |
| | 1.50 | ND | BQL | BQL | 0.13 | 0.15 | 0.23 |
| Total Impurities | | 0.1 | 0.24 | 0.20 | 0.35 | 0.32 | 0.51 |

TABLE 43E

Stability Data for the Formulation # 10A Stored at 40° C. ± 2° C./75% ± 5% RH

| Naloxone | RRT | T = 0 | 1 Month | 2 Months | 6 Months | 12 Months |
|---|---|---|---|---|---|---|
| Physical appearance (Clarity, Color) | | Clear, Colorless | Clear, Colorless | Clear, Colorless | Clear, Pale Yellow | Clear, Pale Yellow |
| Assay (%) | | 100 | 100.39 | 101.31 | 100.46 | 105.26 |
| Naloxone-N-Oxide | | ND | 0.02 | ND | NP | NP |
| Impurity C | 0.53 | ND | 0.01 | ND | ND | ND |
| Impurity A | 0.61 | ND | 0.02 | 0.03 | 0.03 | 0.06 |
| Impurity F | 0.93 | ND | ND | ND | ND | ND |
| Impurity D | 1.14 | ND | ND | 24.57 ppm | NP | NP |
| Impurity E | 1.42 | 0.03 | 0.05 | 0.04 | 0.02 | 0.02 |
| Impurity B | 1.87 | ND | ND | ND | ND | ND |

TABLE 43E-continued

Stability Data for the Formulation # 10A Stored at 40° C. ± 2° C./75% ± 5% RH

| Naloxone | RRT | T = 0 | 1 Month | 2 Months | 6 Months | 12 Months |
|---|---|---|---|---|---|---|
| Unknown Impurities | 0.56 | ND | BQL | BQL | BQL | 0.06 |
|  | 0.61 | ND | ND | ND | 0.05 | ND |
|  | 0.71 | BQL | 0.06 | BQL | BQL | ND |
|  | 0.79 | ND | BQL | BQL | BQL | 0.06 |
|  | 1.07 | 0.07 | 0.05 | 0.06 | 0.06 | 0.07 |
|  | 1.18 | ND | ND | ND | BQL | 0.07 |
|  | 1.27 | ND | ND | 0.07 | 0.07 | ND |
|  | 1.32 | ND | ND | ND | BQL | 0.08 |
|  | 1.50 | ND | 0.05 | 0.08 | 0.22 | 0.24 |
|  | 1.57 | ND | BQL | BQL | BQL | 0.06 |
| Total Impurities |  | 0.1 | 0.26 | 0.28 | 0.45 | 0.72 |

TABLE 43F

Stability Data for the Formulation # 10A Stored at 55° C. ± 2° C.

| Naloxone | RRT | T = 0 | 1 Week | 2 Weeks | 1 Month | 2 Months |
|---|---|---|---|---|---|---|
| Physical appearance (Clarity, Color) |  | Clear, Colorless | Clear, Colorless | Clear, Light yellow | Clear, Light yellow | Clear, yellow |
| Assay (%) |  | 100 | 98.48 | 102.74 | 101.14 | 103.18 |
| Naloxone-N-oxide (%) |  | ND | ND | 0.04 | 0.02 | NP |
| Impurity C | 0.53 | ND | ND | 0.01 | 0.02 | 0.01 |
| Impurity A | 0.61 | ND | 0.03 | 0.04 | 0.05 | 0.07 |
| Impurity F | 0.93 | ND | ND | ND | ND | ND |
| Impurity D | 1.14 | ND | ND | 3.18 ppm | NP | NP |
| Impurity E | 1.42 | 0.03 | 0.04 | 0.02 | 0.02 | 0.04 |
| Impurity B | 1.87 | ND | ND | ND | ND | ND |
| Unknown Impurities | 0.71 | BQL | 0.07 | BQL | BQL | BQL |
|  | 1.07 | 0.07 | 0.09 | 0.07 | 0.06 | 0.09 |
|  | 1.16 | ND | ND | BQL | BQL | 0.05 |
|  | 1.30 | ND | ND | BQL | 0.05 | BQL |
|  | 1.32 | ND | ND | ND | BQL | 0.06 |
|  | 1.50 | ND | BQL | 0.05 | 0.10 | 0.13 |
|  | 1.59 | ND | ND | ND | BQL | 0.05 |
|  | 1.62 | ND | ND | ND | BQL | 0.07 |
|  | 1.63 | ND | ND | ND | ND | 0.07 |
|  | 1.73 | ND | ND | BQL | BQL | 0.05 |
| Total Impurities |  | 0.1 | 0.23 | 0.23 | 0.32 | 0.69 |

TABLE 43G

Stability Data for the Formulation #11A Stored at 25° C. ± 2° C./60% ± 5% RH

| Naloxone | RRT | T = 0 | 1 Month | 2 Months | 6 months | 9 months | 12 months |
|---|---|---|---|---|---|---|---|
| Physical appearance (Clarity, Color) |  | Clear, Colorless | Clear, Colorless | Clear, Colorless | Clear, Colorless | Clear, Colorless | Clear, Colorless |
| Assay (%) |  | 100 | 98.9 | 101.55 | 97.63 | NP | 103.68 |
| Naloxone-N-oxide |  | ND | ND | ND | ND | NP | NP |
| Impurity C | 0.53 | ND | ND | ND | ND | 0.02 | 0.01 |
| Impurity A | 0.63 | ND | ND | ND | ND | 0.03 | 0.02 |
| Impurity F | 0.93 | ND | ND | ND | ND | ND | ND |
| Impurity D | 1.14 | ND | ND | ND | NP | NP | NP |
| Impurity E | 1.42 | 0.05 | 0.04 | 0.04 | 0.05 | 0.02 | 0.02 |
| Impurity B | 1.87 | ND | ND | ND | ND | ND | ND |
|  | 1.07 | 0.07 | 0.08 | 0.1 | 0.06 | 0.05 | 0.08 |
|  | 1.32 | ND | ND | ND | ND | ND | 0.06 |
|  | 1.50 | ND | 0.07 | 0.11 | 0.36 | 0.41 | 0.48 |
| Total Impurities |  | 0.12 | 0.19 | 0.25 | 0.47 | 0.53 | 0.67 |

TABLE 43H

Stability Data for the Formulation #11A Stored at 40° C. ± 2° C./75% ± 5% RH

| Naloxone | RRT | T = 0 | 1 Month | 2 Months | 6 months | 12 months |
|---|---|---|---|---|---|---|
| Physical appearance (Clarity, Color) | | Clear, Colorless | Clear, Colorless | Clear, Colorless | Clear, Pale Yellow | Clear, Pale Yellow |
| Assay (%) | | 100 | 100.65 | 99.4 | 97.17 | 99.67 |
| Naloxone-N-oxide | | ND | 0.02 | NP | NP | NP |
| Impurity C | 0.53 | ND | ND | ND | ND | ND |
| Impurity A | 0.63 | ND | 0.01 | ND | 0.04 | 0.03 |
| Impurity F | 0.93 | ND | ND | ND | ND | ND |
| Impurity D | 1.14 | ND | ND | 16.35 ppm | NP | NP |
| Impurity E | 1.42 | 0.05 | 0.04 | 0.14 | 0.04 | 0.03 |
| Impurity B | 1.87 | ND | ND | ND | ND | ND |
| Unknown Impurities | 0.56 | ND | BQL | ND | 0.06 | 0.1 |
| | 0.71 | BQL | 0.05 | BQL | 0.05 | BQL |
| | 0.75 | ND | BQL | BQL | 0.05 | 0.06 |
| | 0.79 | ND | BQL | BQL | 0.05 | 0.08 |
| | 1.07 | 0.07 | 0.05 | 0.08 | 0.06 | 0.07 |
| | 1.18 | ND | ND | ND | BQL | 0.09 |
| | 1.30 | ND | ND | ND | 0.08 | 0.14 |
| | 1.50 | ND | 0.14 | 0.21 | 0.32 | 0.31 |
| | 1.57 | ND | ND | ND | ND | 0.06 |
| | 1.59 | ND | ND | ND | ND | 0.08 |
| | 1.62 | ND | ND | ND | ND | 0.1 |
| | 1.63 | ND | ND | ND | ND | 0.1 |
| Total Impurities | | 0.12 | 0.29 | 0.43 | 0.75 | 1.25 |

TABLE 43I

Stability Data for the Formulation # 11A Stored at 55° C. ± 2° C.

| Naloxone | RRT | T = 0 | 1 Week | 2 Weeks | 1 Month | 2 Months |
|---|---|---|---|---|---|---|
| Physical appearance (Clarity, Color) | | Clear, Colorless | Clear, Colorless | Clear, Light yellow | Clear, yellow | Clear, yellow |
| Assay (%) | | 100 | 98.11 | 98.89 | 99.96 | 100.34 |
| Naloxone-N-oxide | | ND | ND | 0.05 | 0.03 | NP |
| Impurity C | 0.53 | ND | 0.01 | 0.01 | 0.01 | 0.01 |
| Impurity A | 0.63 | ND | 0.02 | 0.02 | 0.03 | 0.03 |
| Impurity F | 0.93 | ND | ND | ND | ND | ND |
| Impurity D | 1.14 | ND | ND | 2.31 ppm | NP | NP |
| Impurity E | 1.42 | 0.05 | 0.04 | 0.02 | 0.01 | 0.02 |
| Impurity B | 1.87 | ND | ND | ND | ND | ND |
| Unknown Impurities | 0.56 | ND | BQL | BQL | BQL | 0.06 |
| | 0.71 | BQL | 0.05 | BQL | BQL | BQL |
| | 0.75 | ND | ND | BQL | BQL | 0.05 |
| | 1.07 | 0.07 | 0.07 | 0.07 | 0.07 | 0.07 |
| | 1.27 | ND | ND | ND | BQL | 0.08 |
| | 1.30 | ND | ND | BQL | BQL | 0.05 |
| | 1.39 | ND | ND | BQL | BQL | 0.05 |
| | 1.50 | ND | 0.1 | 0.14 | 0.17 | 0.18 |
| Total Impurities | | 0.12 | 0.29 | 0.31 | 0.32 | 0.6 |

NP = Not Performed
ND = Not Detected
ppm = parts per million

The data suggest that formulation #9A, #10A, and #11A demonstrates satisfactory stability with no significant increase in individual or total impurities. Based upon these results, the formulation containing 0.02% w/w of sodium ascorbate as an antioxidant and 0.001% edetate disodium dihydrate as a chelating agent is chemically stable. Additionally, formulations containing 0.01% and 0.005% edetate disodium dihydrate as a chelating agent are chemically stable.

Example 14. Intranasal and Sublingual Administration of Naloxone Spray Formulations Method Protocol design was a Phase I, open-label, randomized, single-dose, five-way crossover study. The study assessed the bioavailability of a single 8 milligrams and 16 milligrams dose of naloxone in a formulation of the present invention either intranasally or sublingually to a single 0.4 milligram intramuscular dose of naloxone under fasted conditions. 145 subjects were randomly assigned to one of five groups including 8 milligrams sublingual dose, 16 milligrams sublingual dose, 8 milligrams intranasal dose, 16 milligrams intranasal dose and 0.4 milligram naloxone dose. Plasma concentrations were taken at pre-dose, 0.03, 0.07, 0.1, 0.13, 0.17, 0.25, 0.5, 1, 2 4, 8 and 12 hours' post-dose.

Results

As seen in Table 31 below each of intranasal administration and sublingual administration resulted in significantly greater plasma concentrations than intramuscular administration at all time points tested up to 1 hour after administration. Further intranasal administration of naloxone resulted in significantly greater plasma concentration than sublingual administration at all times points tested up to 1 hour after administration.

However, at 2 and 4 hours post-dose the mean plasma concentration of naloxone in subjects that were intranasally administered 16 milligrams of naloxone was significantly lower than that for those subject that were sublingually administered 16 milligrams of naloxone. The same pattern was found with those subjects administered 8 milligram doses of naloxone.

Further, peak concentration in plasma ($C_{max}$) and area under the concentration-time curve from time-zero to 1 hour post dose (AUC) followed the exact same pattern as described above for mean plasma concentrations.

TABLE 44

Mean Plasma Concentration for 8 mg and 16 mg Intranasal and Sublingual Administration

| Parameters* | 8 mg SL | 8 mg IN | 16 mg SL | 16 mg IN | 0.4 mg IM |
|---|---|---|---|---|---|
| N | 29 | 28 | 29 | 29 | 30 |
| Conc. @ 0.03 h (ng/mL) | 0.18 ± 0.29 | 6.19 ± 14.47 | 0.52 ± 0.8 | 9.29 ± 14.31 | 0.15 ± 0.29 |
| Conc. @ 0.07 h (ng/mL) | 0.62 ± 0.96 | 13.95 ± 19.06 | 1.69 ± 1.85 | 29.69 ± 28.01 | 0.36 ± 0.38 |
| Conc. @ 0.1 h (ng/mL) | 0.88 ± 0.94 | 18.75 ± 15.61 | 2.31 ± 2.08 | 46.34 ± 36.64 | 0.51 ± 0.41 |
| Conc. @ 0.13 h (ng/mL) | 1.17 ± 1.13 | 20.48 ± 13.11 | 3.16 ± 3.39 | 49.31 ± 33.98 | 0.58 ± 0.39 |
| Conc. @ 0.17 h (ng/mL) | 1.54 ± 1.1 | 19.96 ± 10.73 | 3.63 ± 3.83 | 45.77 ± 24.58 | 0.63 ± 0.36 |
| Conc. @ 0.25 h (ng/mL) | 1.98 ± 1.29 | 16.49 ± 6.71 | 4.39 ± 4.24 | 35.04 ± 13.23 | 0.69 ± 0.4 |
| Conc. @ 0.5 h (ng/mL) | 2.03 ± 1.28 | 9.88 ± 4.42 | 3.94 ± 2.96 | 22.35 ± 8.19 | 0.62 ± 0.22 |
| Conc. @ 1 h (ng/mL) | 1.61 ± 0.85 | 6.29 ± 2.7 | 2.96 ± 1.66 | 14.07 ± 5.61 | 0.51 ± 0.16 |
| $C_{max}$ (ng/mL) | 2.03 | 20.48 | 4.39 | 49.31 | 0.69 |
| AUC @ 1 h (ng * h/mL) | 1.68 | 11.18 | 3.42 | 24.91 | 0.57 |

*Mean ± Standard Deviation
SL denotes sublingual administration
IN denotes intranasal administration
IM denotes intramuscular administration
N denotes number of subjects tested
h denotes hours

Example 15. Bioavailability of Naloxone Nasal Spray

Method

Protocol design was a Phase I, open-label, randomized, three-treatment, 6-sequence, 3-way crossover study, comparative bioavailability study of naloxone nasal spray and naloxone hydrochloride intramuscular injection in healthy volunteers. The study compared early exposures (plasma concentrations at each time point and partial AUCs) up to 1 hour following a single dose of two test formulations of naloxone nasal spray (8 mg/spray with 20% alcohol and 8 mg/spray with 50% alcohol) with the reference formulation of naloxone hydrochloride (HCl) intramuscular (IM) Injection (0.4 mg/mL) under fasted conditions.

This study consisted of four periods, a Screening Period and three Treatment Periods. During Screening (Day −28 to Day −1), subjects signed the informed consent and eligibility was determined. Twenty-four (24) subjects received a single dose of study drug administered on Day 1 (Period 1), Day 5 (Period 2), and Day 9 (Period 3) following an overnight fast of at least 10 hours. Subjects were confined before dosing to ensure adherence to the 10-hour fast and remained confined until all study procedures were completed on Day 10. No food was allowed until 4 hours after each dose administration. Meals were provided at scheduled times.

In each treatment period, blood samples (1×10 mL) pharmacokinetic (PK) analyses were collected in a Vacutainer tube containing K2 EDTA as a preservative at 0 hour (predose), 2, 4, 6, 8, 10, 15, 30, and 45 minutes, and at 1, 2, 4, 8, 12, and 24 hours post dose (15 time points). Blood (plasma) samples were analyzed for unconjugated naloxone and total naloxone using validated LC/MS/MS assays. Safety and tolerability were assessed throughout the study. Treatment A was 8 milligrams of naloxone in 20% ethyl alcohol administered as a nasal spray. Treatment B was 8 milligrams of naloxone in 50% ethyl alcohol administered as a nasal spray. Treatment C was 0.4 milligrams of naloxone hydrochloride administered in a 1 milliliter intramuscular injection.

Statistical Methods:

Arithmetic means, standard deviations, median, minimum, maximum, and coefficients of variation were calculated for all pharmacokinetic parameters. Additionally, geometric means were calculated for plasma concentrations and geometric means and geometric CV % were reported for Cmax and AUCs.

Analyses of variance (ANOVA) with effects for sequence, subject nested within sequence, period, and treatment were performed on the ln-transformed plasma concentrations at each time point up to 1 hour postdose and the ln-transformed PK parameters such as AUC0-t, AUC0-inf, partial AUCs, and Cmax. Each ANOVA included calculation of least-squares means (LSMs), the differences between adjusted means, and the standard error associated with these differences. Ratios of means were calculated using the LSM for ln-transformed plasma concentrations at each time point up to 1 hour post dose and ln transformed AUC0-t, AUC0-inf, partial AUCs, and Cmax.

The comparative bioavailability of unconjugated naloxone and total naloxone between each of the two test (Naloxone IN Spray [8 mg/spray with 20% alcohol] and Naloxone IN Spray [8 mg/spray with 50% alcohol]) and reference (Naloxone Hydrochloride IM Injection [0.4 mg/mL]) formulations were investigated using the point estimates (test/reference ratios of means) and the corresponding 90% confidence intervals (CIs) for plasma concentrations at each time point up to 1 hours post dose and AUC0 t, AUC0-inf, partial AUCs, and Cmax. The CIs were expressed as a percentage relative to the LSM.

Pharmacokinetic and statistical analyses were performed using appropriate software, e.g. Phoenix™ WinNonlin® (Version 6.3, Pharsight Corporation) and SAS® (Version 9.4, SAS Institute Inc.).

Statistical Analysis

No values for AUC0-inf, $\lambda z$, and $t\frac{1}{2}$ were reported for cases that did not exhibit a terminal log linear phase in the concentration-time data.

The elimination rate constant, $\lambda z$, was calculated as the negative of the slope of the terminal log linear segment of the plasma concentration-time curve; the range of data used was determined by visual inspection of a semi-logarithmic plot of concentration vs. time. Elimination half-life ($t\frac{1}{2}$) was calculated according to the following equation: $t\frac{1}{2}=0.693/\lambda Z$.

Area under the curve to the final sample with a concentration greater than the limit of quantification (LOQ [AUC0-t]) was calculated using the linear trapezoidal method and extrapolated to infinity using:

$$AUC0\text{-}inf = AUC0\text{-}t + Clast/\lambda Z, \text{ where Clast is the final concentration} \geq LOQ.$$

Statistical analysis of pharmacokinetic data was performed using appropriate software, e.g., Phoenix™ WinNonlin® (Version 6.3 Pharsight Corporation) and SAS® (Version 9.4, SAS Institute Inc.).

TABLE 46

Mean Plasma Concentrations of Unconjugated Naloxone through 1 Hour after Administration of Naloxone Nasal Spray 8 mg (20% alcohol) (Treatment A), Naloxone Nasal Spray 8 mg (50% alcohol) (Treatment B), and Naloxone HCL IM Injection 0.4 mg (Treatment C)

| Treatment Description | n | 2 min Mean | 4 min Mean | 6 min Mean | 8 min Mean | 10 min Mean | 15 min Mean | 30 min Mean | 45 min Mean | 60 min Mean |
|---|---|---|---|---|---|---|---|---|---|---|
| Naloxone Nasal Spray 8 mg (20% alcohol) | 24 | 0.725 | 3.84 | 6.87 | 8.07 | 9.64 | 10.7 | 8.44 | 6.59 | 5.83 |
| Naloxone Nasal Spray 8 mg (50% alcohol) | 24 | 2.77 | 11.8 | 21.3 | 22.6 | 25.8 | 23.9 | 15.4 | 11.1 | 9.06 |
| Naloxone HCL IM Injection 0.4 mg | 24 | 0.0527 | 0.241 | 0.420 | 0.547 | 0.660 | 0.792 | 0.699 | 0.628 | 0.570 |

Note:
Mean concentrations reported in ng/mL to 3 significant figures
IM = intramuscular administration

TABLE 47

Mean Partial AUCs of Unconjugated Naloxone through 1 Hour after Administration of Naloxone Nasal Spray 8 mg (20% alcohol) (Treatment A), Naloxone Nasal Spray 8 mg (50% alcohol) (Treatment B), and Naloxone HCL IM Injection 0.4 mg (Treatment C)

| Treatment Description | n | AUC 2 min Mean | AUC 4 min Mean | AUC 6 min Mean | AUC 8 min Mean | AUC 10 min Mean | AUC 15 min Mean | AUC 30 min Mean | AUC 45 min Mean | AUC 60 min Mean |
|---|---|---|---|---|---|---|---|---|---|---|
| Naloxone Nasal Spray 8 mg (20% alcohol) | 24 | 0.0116 | 0.0860 | 0.257 | 0.502 | 0.809 | 1.64 | 4.03 | 5.90 | 7.45 |
| Naloxone Nasal Spray 8 mg (50% alcohol) | 24 | 0.0458 | 0.286 | 0.826 | 1.53 | 2.34 | 4.36 | 9.06 | 12.3 | 14.8 |
| Naloxone HCL IM Injection 0.4 mg | 24 | 0.000877 | 0.00553 | 0.0164 | 0.0322 | 0.0526 | 0.113 | 0.298 | 0.463 | 0.612 |

Note:
Partial AUCs reported in h*ng/mL to 3 significant figures
IM = intramuscular administration Results As seen in Table 46, the mean unconjugated naloxone concentrations after the administration of naloxone spray 8 mg with 20% alcohol and with 50% alcohol were appreciably higher than those observed after the administration of naloxone HCl 0.4 mg IM at all timepoints from 2 minutes through 1 h postdose. Additionally, mean unconjugated naloxone concentrations after the administration of naloxone spray 8 mg with 50% alcohol were higher than those observed after the administration of naloxone spray 8 mg with 20% alcohol at all timepoints from 2 minutes through 1 h postdose, suggesting the higher alcohol percentage enhanced the relative bioavailability of the naloxone spray product.

As seen in Table 47, a similar trend was observed for partial areas calculated through 1 hour postdose. the mean partial unconjugated naloxone AUCs after the administration of naloxone spray 8 mg with 20% alcohol or with 50% alcohol were appreciably higher than those observed after the administration of naloxone HCl 0.4 mg IM at all timepoints from 2 minutes through 1 h postdose.

The mean partial unconjugated naloxone AUCs after the administration of the naloxone spray 8 mg with 50% alcohol were higher than those observed after the administration of naloxone spray 8 mg with 20% alcohol at all timepoints from 2 minutes through 1 h postdose. An increase in alcohol percentage resulted in an increase in unconjugated naloxone systemic exposure following administration of the naloxone spray product.

Thus, nasal administration of compositions of the present invention result in faster plasma accumulation of naloxone and a higher overall plasma concentration at earlier time points than injection of similar doses of naloxone. The faster onset and higher overall plasma concentrations are critical to those that have experienced an opioid overdose as the subject could die within minutes of the overdose.

Example 16. Bioavailability of Naloxone Nasal Spray Versus IV and IM Injection

Method

Protocol design was a Phase I, open-label, randomized, four-treatment, 4-way crossover study, comparative bioavailability study of naloxone nasal spray, naloxone hydrochloride intramuscular injection and naloxone hydrochloride intravenous injection in healthy volunteers. The study compared early exposures (plasma concentrations at each time point and partial AUCs) up to 1 hour following a single dose of two test formulations of naloxone nasal spray (8 mg/spray with 20% alcohol and 8 mg/spray with 50% alcohol) with the reference formulation of naloxone hydrochloride (HCl) intramuscular (IM) Injection (0.4 mg/mL) and a reference formulation of naloxone HCl intravenous injection (1 mg/mL) under fasted conditions.

This study consisted of five periods, a Screening Period and four Treatment Periods. During Screening (Day −28 to Day −1), subjects signed the informed consent and eligibility was determined. Twenty-four (24) subjects received a single dose of study drug administered on Day 1 (Period 1), Day 5 (Period 2), Day 9 (Period 3 and Day 13 (Period 4) following an overnight fast of at least 10 hours. Subjects were confined before dosing to ensure adherence to the 10-hour fast and remained confined until all study procedures were completed on Day 14. No food was allowed until 4 hours after each dose administration. Meals were provided at scheduled times.

In each treatment period, blood samples (1×10 mL) pharmacokinetic (PK) analyses were collected in a Vacutainer tube containing K2 EDTA as a preservative at 0 hour (predose), 2, 4, 6, 8, 10, 15, 30, and 45 minutes, and at 1, 2, 4, 8, 12, and 24 hours post dose (15 time points). Blood (plasma) samples were analyzed for unconjugated naloxone and total naloxone using validated LC/MS/MS assays. Safety and tolerability were assessed throughout the study. Treatment A was 8 milligrams of naloxone in 20% ethyl alcohol administered as a nasal spray. Treatment B was 8 milligrams of naloxone in 50% ethyl alcohol administered as a nasal spray. Treatment C was 2.0 milligrams of naloxone hydrochloride administered in a 2-milliliter intravenous injection. Treatment D was 0.4 milligrams of naloxone hydrochloride administered in a 1 milliliter intramuscular injection.

Statistical Methods:

Arithmetic means, standard deviations, median, minimum, maximum, and coefficients of variation were calculated for all pharmacokinetic parameters. Additionally, geometric means were calculated for plasma concentrations and geometric means and geometric CV % were reported for Cmax and AUCs.

Analyses of variance (ANOVA) with effects for sequence, subject nested within sequence, period, and treatment were performed on the ln-transformed plasma concentrations at each time point up to 1 hour postdose and the ln-transformed PK parameters such as AUC0-t, AUC0-inf, partial AUCs, and Cmax. Each ANOVA included calculation of least-squares means (LSMs), the differences between adjusted means, and the standard error associated with these differences. Ratios of means were calculated using the LSM for ln-transformed plasma concentrations at each time point up to 1 hour post dose and ln transformed AUC0-t, AUC0-inf, partial AUCs, and Cmax.

The comparative bioavailability of unconjugated naloxone and total naloxone between each of the two test (Naloxone IN Spray [8 mg/spray with 20% alcohol] and Naloxone IN Spray [8 mg/spray with 50% alcohol]) and reference (Naloxone Hydrochloride IM Injection [0.4 mg/mL]) formulations were investigated using the point estimates (test/reference ratios of means) and the corresponding 90% confidence intervals (CIs) for plasma concentrations at each time point up to 1 hours post dose and AUC0 t, AUC0-inf, partial AUCs, and Cmax. The CIs were expressed as a percentage relative to the LSM.

Pharmacokinetic and statistical analyses were performed using appropriate software, e.g. Phoenix™ WinNonlin® (Version 6.3, Pharsight Corporation) and SAS® (Version 9.4, SAS Institute Inc.).

Statistical Analysis

No values for AUC0-inf, $\lambda z$, and $t\frac{1}{2}$ were reported for cases that did not exhibit a terminal log linear phase in the concentration-time data.

The elimination rate constant, $\lambda z$, was calculated as the negative of the slope of the terminal log linear segment of the plasma concentration-time curve; the range of data used was determined by visual inspection of a semi-logarithmic plot of concentration vs. time. Elimination half-life ($t\frac{1}{2}$) was calculated according to the following equation: $t\frac{1}{2}=0.693/\lambda Z$.

Area under the curve to the final sample with a concentration greater than the limit of quantification (LOQ [AUC0-t]) was calculated using the linear trapezoidal method and extrapolated to infinity using:

$$AUC0\text{-}inf = AUC0\text{-}t + Clast/\lambda Z, \text{ where } Clast \text{ is the final concentration} \geq LOQ.$$

Statistical analysis of pharmacokinetic data was performed using appropriate software, e.g., Phoenix™ WinNonlin® (Version 6.3 Pharsight Corporation) and SAS® (Version 9.4, SAS Institute Inc.).

TABLE 48

Mean Plasma Concentrations of Unconjugated Naloxone through 2 Hour after Administration of Naloxone Nasal Spray 8 mg (20% alcohol) (Treatment A), Naloxone Nasal Spray 8 mg (50% alcohol) (Treatment B), Naloxone HCl IV Injection 2.0 mg and Naloxone HCL IM Injection 0.4 mg (Treatment D)

| Treatment Description | n | 2 min Mean | 4 min Mean | 6 min Mean | 8 min Mean | 10 min Mean | 15 min Mean | 30 min Mean | 45 min Mean | 60 min Mean | 120 min Mean |
|---|---|---|---|---|---|---|---|---|---|---|---|
| Naloxone Nasal Spray 8 mg (20% alcohol) | 23 | 0.635 | 3.58 | 5.87 | 8.32 | 9.68 | 10.2 | 9.84 | 8.20 | 6.89 | 3.09 |
| Naloxone Nasal Spray 8 mg (50% alcohol) | 24 | 2.71 | 9.58 | 16.1 | 20.0 | 21.3 | 21.9 | 15.2 | 11.6 | 9.15 | 3.97 |
| Naloxone HCL IV Injection 2.0 mg | 24 | 24.3 | 16.2 | 12.4 | 10.7 | 9.82 | 8.32 | 6.47 | 4.79 | 3.88 | 1.68 |
| Naloxone HCL IM Injection 0.4 mg | 23 | 0.0734 | 0.263 | 0.455 | 0.573 | 0.69 | 0.826 | 0.771 | 0.686 | 0.642 | 0.379 |

Note:
Mean concentrations reported in ng/mL to 3 significant figures
IM = intramuscular administration
IV = intravenous administration

TABLE 49

Mean Partial AUCs of Unconjugated Naloxone through 2 Hour after Administration of Naloxone Nasal Spray 8 mg (20% alcohol) (Treatment A), Naloxone Nasal Spray 8 mg (50% alcohol) (Treatment B), Naloxone HCl IV Injection 2.0 mg and Naloxone HCL IM Injection 0.4 mg (Treatment D)

| Treatment Description | n | AUC 2 min Mean | AUC 4 min Mean | AUC 6 min Mean | AUC 8 min Mean | AUC 10 min Mean | AUC 15 min Mean | AUC 30 min Mean | AUC 45 min Mean | AUC 60 min Mean | AUC 120 min Mean |
|---|---|---|---|---|---|---|---|---|---|---|---|
| Naloxone Nasal Spray 8 mg (20% alcohol) | 24 | 0.00567 | 0.0541 | 0.174 | 0.371 | 0.647 | 1.42 | 3.82 | 6.01 | 7.81 | 12.3 |
| Naloxone Nasal Spray 8 mg (50% alcohol) | 24 | 0.0220 | 0.172 | 0.507 | 1.00 | 1.62 | 3.28 | 7.63 | 10.8 | 13.2 | 19.1 |
| Naloxone HCL IV Injection 2.0 mg | 24 | 0.302 | 0.879 | 1.36 | 1.75 | 2.11 | 2.87 | 4.67 | 6.01 | 7.05 | 9.60 |
| Naloxone HCL IM Injection 0.4 mg | 23 | NC | 0.00513 | 0.0153 | 0.0304 | 0.0500 | 0.108 | 0.297 | 0.472 | 0.633 | 1.13 |

Note:
Partial AUCs reported in h*ng/mL to 3 significant figures
IM = intramuscular administration
IV = intravenous administration
NC = not calculated due to zero value AUC for one subject in Treatment D

TABLE 50

Mean +/− SD (CV %) [Geometric Mean] Plasma Pharmacokinetic Parameters of Unconjugated Naloxone

| | Treatment | | | |
|---|---|---|---|---|
| | A | B | C | D |
| Formulation/Route | Naloxone Nasal Spray (20% alcohol) | Naloxone Nasal Spray (50% alcohol) | Naloxone IV (1 mg/mL) | Naloxone IM (0.4 mg/mL) |
| Dose (mg) | 8 | 8 | 2 | 0.4 |
| n | 23(19) | 24(20) | 24(24) | 23(23) |
| $C_{max}$ (ng/mL) | 12.8 ± 4.73 (37.0)[12.0] | 25.6 ± 11.4 (44.5)[23.1] | 26.2 ± 21.6 (82.4)[20.8] | 0.91 ± 0.335 (36.8)[0.857] |
| Conc. @ 0 min (ng/mL) | 0.00 | 0.00 | 53.9 ± 85.0 (158)[24.4] | 0.00500 |
| Tmax (h) | 0.250 (0.10-1.00) | 0.250 (0.10-0.50) | 0.0500 (0.0333-1.0) | 0.250 (0.100-1.00) |
| $AUC_{(0-0.25)}$ (ng * h/mL) | 1.60 ± 0.808 (50.5)[1.42] | 3.75 ± 1.97 (52.6)[3.28] | 3.01 ± 1.09 (36.2)[2.87] | 0.119 ± 0.0528 (44.3)[0.108] |
| $AUC_{(0-2)}$ (ng*/mL) | 12.9 ± 4.17 (32.2)[12.3] | 20.4 ± 7.11 (34.9)[19.1] | 9.95 ± 2.96 (29.7)[9.60] | 1.16 ± 0.320 (27.4)[1.13] |
| $AUC_{last}$ (ng * min/mL) | 18.4 ± 6.13 (33.4)[17.4] | 27.3 ± 8.63 (31.6)[25.9] | 12.7 ± 3.51 (27.6)[12.3] | 1.95 ± 0.427 (21.9)[1.90] |
| $AUC_{(0-inf)}$ (ng * min/mL) | 19.0 ± 6.21 (32.7)[18.0] | 28.3 ± 8.00 (28.3)[27.1] | 12.8 ± 3.52 (27.5)[12.3] | 1.95 ± 0.427 (21.9)[1.90] |
| $t_{1/2}$(h) | 1.76 ± 0.697 (39.7)[1.66] | 2.03 ± 1.58 (77.8)[1.73] | 1.22 ± 0.201 (16.4)[1.21] | 1.40 ± 0.543 (38.9)[1.34] |
| CL or CL/F (L/h) | 468 ± 164 (35.0)[443] | 310 ± 111 (35.9)[295] | 167 ± 40.3 (24.1)[162] | 215 ± 48.3 (22.4)[210] |
| Vz or Vz/F | 1130 ± 432 (38.3)[1060] | 954 ± 986 (103)[737] | 297 ± 94.7 (31.9)[282] | 432 ± 165 (38.2)[406] |

TABLE 51

Mean +/− SD (CV %) [Geometric Mean] Plasma Pharmacokinetic Parameters of Total Naloxone

| | Treatment | | | |
|---|---|---|---|---|
| | A | B | C | D |
| Formulation/Route | Naloxone Nasal Spray (20% alcohol) | Naloxone Nasal Spray (50% alcohol) | Naloxone IV (1 mg/mL) | Naloxone IM (0.4 mg/mL) |
| Dose (mg) | 8 | 8 | 2 | 0.4 |
| $N^a$ | 23 (21) | 24 (20) | 24 (21) | 23 (23) |
| $C_{max}$ (ng/mL) | 39.9 ± 19.8 (49.5) [35.6] | 44.5 ± 12.0 (27.0) [43.0] | 29.3 ± 18.8 (64.2) [25.9] | 1.66 ± 0.480 (28.9) [1.60] |
| $T_{max}^b$ (h) | 1.00 (0.25-2.00) | 0.500 (0.100-2.00) | 0.100 (0.0333-0.500) | 0.500 (0.167-1.00) |
| $AUC_{0-0.25}$ (ng · h/mL) | 2.33 ± 1.05 (45.2) [2.11] | 5.32 ± 2.50 (46.9) [4.80] | 4.67 ± 1.29 (27.5) [4.53] | 0.159 ± 0.0645 (40.5) [0.147] |
| $AUC_{0-2}$ (ng · h/mL) | 50.4 ± 18.4 (36.6) [46.8] | 57.1 ± 15.7 (27.4) [55.0] | 20.5 ± 4.21 (20.5) [20.1] | 2.44 ± 0.574 (23.5) [2.38] |
| $AUC_{last}$ (ng · h/mL) | 114 ± 38.3 (33.6) [107] | 116 ± 30.6 (26.4) [112] | 35.2 ± 7.37 (21.0) [34.4] | 5.25 ± 1.12 (21.4) [5.12] |
| $AUC_{0-inf}$ (ng · h/mL) | 120 ± 40.2 (33.6) [112] | 117 ± 32.5 (27.7) [113] | 37.0 ± 7.69 (20.8) [36.1] | 5.57 ± 1.18 (21.2) [5.44] |
| $t_{1/2}$ (h) | 5.14 ± 1.38 (26.8) [4.98] | 5.31 ± 1.26 (23.7) [5.17] | 4.98 ± 1.59 (32.0) [4.70] | 3.00 ± 1.18 (39.4) [2.86] |

Results

Figure 2:
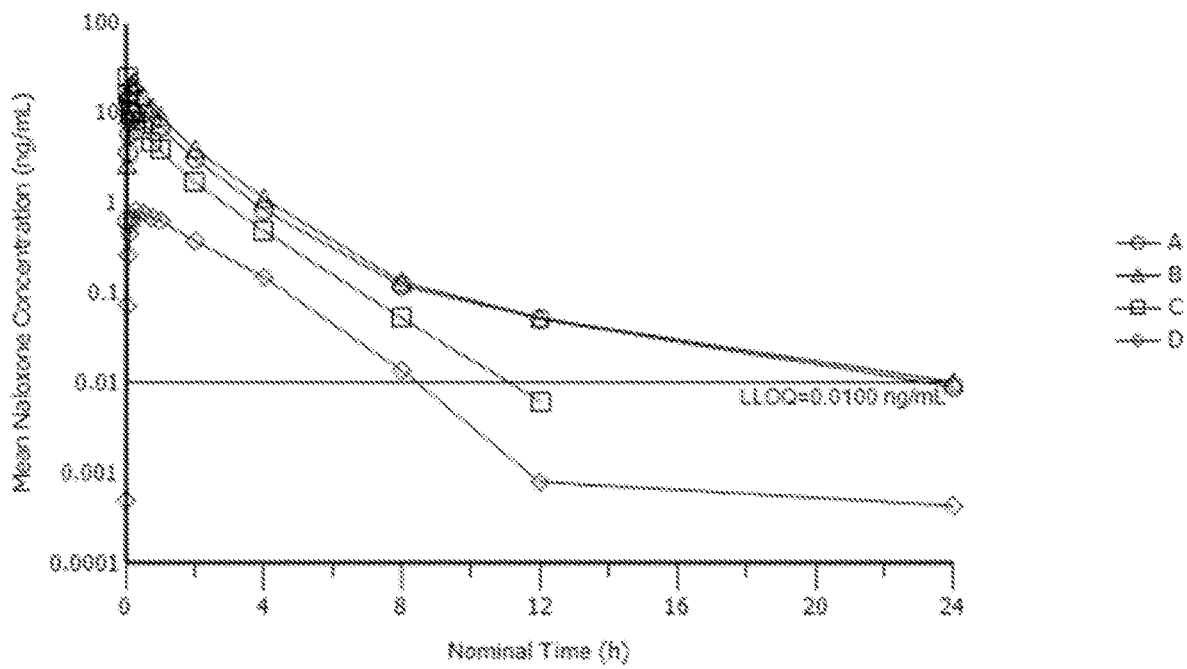
FIG. 2. Mean plasma concentration of Treatments A-D. Values based on a geometric mean.

As seen in Table 50, following a single 8 mg dose of two test formulations (treatments A and B) of Naloxone Nasal Spray containing 20% alcohol or 50% alcohol versus a single 2 mg IV or 0.4 mg IM, unconjugated naloxone was rapidly absorbed into systemic circulation with a median Tmax of 15 min for both of the test formulations, which is comparable to the Tmax after a single dose of 0.4 mg IM Naloxone. The mean unconjugated naloxone concentrations after the administration of the two test formulations were appreciably higher than those observed after the administration of the IM dose at all timepoints from 2 minutes (0.635 and 2.71 ng/mL versus 0.0734 ng/mL) through 24 h postdose. See, Table 48 and FIG. 2. The geometric mean values of unconjugated naloxone exposure (Cmax, AUClast, AUC0-inf) generated from the Naloxone Nasal Spray formulations were 9.6- to 27-fold higher compared to Naloxone 0.4 mg IM. See, Table 50.

Unconjugated naloxone geometric mean Cmax after administration of Naloxone Nasal Spray formulations was similar (1.1-fold for the Nasal Spray in 50% alcohol) or lower (0.58-fold for the Nasal Spray in 20% alcohol) compared to the observed Cmax at 2 min postdose (the first postdose sampling time) after administration of Naloxone 2 mg IV. See, Table 50. In addition, the observed Cmax for both test formulations was lower than the estimated C0 (geometric mean of 24.4 ng/mL) for the 2 mg IV. The geometric mean AUClast and AUC0-inf of unconjugated naloxone generated from the two test formulations were 1.4- to 2.2-fold higher compared to Naloxone 2 mg IV. The Naloxone Nasal Spray in 50% alcohol achieved 1.5- to 1.9-fold higher unconjugated naloxone exposure levels than the Naloxone Nasal Spray in 20% alcohol. Unconjugated naloxone was eliminated rapidly with a geometric mean terminal t½ less than 2 h for all study formulations.

Total naloxone exposure (Cmax, AUClast, AUC0-inf) was from 21- to 27-fold higher for the two test formulations compared to the 0.4 mg IM, and 1.4- to 3.3-fold higher compared to the 2 mg IV injection. See, Table 51. In general, comparable total naloxone exposure was observed between the two test formulations with exposure ratios (Naloxone Nasal Spray in 20% versus 50% alcohol) from 0.83 to 1.0.

Overall, the investigational products were generally well-tolerated in healthy subjects. Although efficacy was not measured in the current study, the pharmacokinetic results demonstrated similar unconjugated naloxone concentration levels for the Naloxone Nasal Spray 8 mg formulations and intravenous naloxone 2 mg, and systemic exposure to unconjugated naloxone was on the same order for both routes of administration.

Thus, nasal administration of compositions of the present invention is as advantageous as intravenous administration.

The invention claimed is:

1. A nasal spray formulation comprising from about 5% to about 15% w/w naloxone or a pharmaceutically acceptable salt thereof, from about 0.001% to about 0.5% w/w of a chelating agent, ethanol, propylene glycol, and water, wherein w/w denotes weight by total weight of the formulation.

2. The formulation of claim 1, wherein the chelating agent is edetate disodium dihydrate.

3. The formulation of claim 1, wherein the ethanol is at a concentration from about 20% to about 50% w/w and the propylene glycol is at a concentration from about 5% to about 10% w/w.

4. The formulation of claim 1, further comprising from about 0.001% to about 0.2% w/w of a permeation enhancer.

5. The formulation of claim 4, wherein the permeation enhancer is benzalkonium chloride.

6. The formulation of claim 1, further comprising one or more pH adjustors.

7. The formulation of claim 1, wherein the pH is from about 3 to about 6.

8. The formulation of claim 1, wherein the pH is from about 4 to about 5.

9. The formulation of claim 1, wherein the naloxone or pharmaceutically acceptable salt thereof, is at a concentration of about 8% w/w.

10. The formulation of claim 1, wherein the water is at a concentration from about 20% to about 95% w/w.

11. A nasal spray formulation comprising from about 5% to about 10% w/w naloxone or a pharmaceutically acceptable salt thereof, from about 0.001% to about 0.5% w/w of a chelating agent, from about 0.005% to about 0.10% w/w of a permeation enhancer, ethanol, propylene glycol, and water, wherein w/w denotes weight by total weight of the formulation.

12. The formulation of claim 11, wherein the permeation enhancer is at a concentration from about 0.01% to about 0.1% w/w.

13. The formulation of claim 11, wherein the chelating agent is edetate disodium dihydrate.

14. The formulation of claim 11, wherein the permeation enhancer is benzalkonium chloride.

15. The formulation of claim 14, wherein the benzalkonium chloride is at a concentration of about 0.01% w/w.

16. The formulation of claim 11, wherein the naloxone or pharmaceutically acceptable salt thereof, is at a concentration of about 8% w/w.

17. The formulation of claim 11, further comprising one or more pH adjustors.

18. The formulation of claim 11, wherein the pH is from about 3 to about 6.

19. The formulation of claim 11, wherein the pH is from about 4 to about 5.

* * * * *